United States Patent
Shadduck

(10) Patent No.: US 9,113,944 B2
(45) Date of Patent: Aug. 25, 2015

(54) METHOD FOR PERFORMING LUNG VOLUME REDUCTION

(71) Applicant: Tsunami MedTech, LLC, Menlo Park, CA (US)

(72) Inventor: John H. Shadduck, Menlo Park, CA (US)

(73) Assignee: Tsunami MedTech, LLC, Menlo Park, CA (US)

( * ) Notice: Subject to any disclaimer, the term of this patent is extended or adjusted under 35 U.S.C. 154(b) by 74 days.

(21) Appl. No.: 13/681,193

(22) Filed: Nov. 19, 2012

(65) Prior Publication Data

US 2013/0079772 A1  Mar. 28, 2013

Related U.S. Application Data

(63) Continuation of application No. 12/255,394, filed on Oct. 21, 2008, now Pat. No. 8,313,485, which is a continuation of application No. 11/244,329, filed on Oct. 5, 2005, now Pat. No. 8,016,823, and a (Continued)

(51) Int. Cl.
*A61B 18/04* (2006.01)
*A61B 17/3203* (2006.01)

(Continued)

(52) U.S. Cl.
CPC ............. *A61B 17/3203* (2013.01); *A61B 18/04* (2013.01); *A61B 18/1492* (2013.01);

(Continued)

(58) Field of Classification Search
CPC ........... A61B 2018/00005; A61B 2018/00011; A61B 2018/00017; A61B 2018/00029; A61B 2018/00345; A61B 2018/00404; A61B 2018/00541; A61B 2018/00549; A61B 2018/044; A61B 2018/048
USPC ..................................................... 606/27–31
See application file for complete search history.

(56) References Cited

U.S. PATENT DOCUMENTS

| 408,899 A | 8/1889 | Bioch et al. |
| 697,181 A | 4/1902 | Smith |

(Continued)

FOREIGN PATENT DOCUMENTS

| WO | WO 00/11927 | 3/2000 |
| WO | WO 00/29055 | 5/2000 |

(Continued)

OTHER PUBLICATIONS

Coda, et al., "Effects of pulmonary reventilation on gas exchange after cryolytic disobstruction of endobronchial tumors," *Minerva Medical*, vol. 72, pp. 1627-1631, Jun. 1981 (with English translation).

(Continued)

*Primary Examiner* — Ronald Hupczey, Jr.
(74) *Attorney, Agent, or Firm* — Levine Bagade Han LLP

(57) ABSTRACT

This invention relates to surgical instruments for applying energy to tissue. In one embodiment, an elongated introducer has a handle portion that includes an interior chamber that is supplied with a biocompatible liquid under pressure. An energy source causes a liquid-to-vapor phase change within the interior chamber and ejects a flow of vapor media from the working end of the introducer. The flow of vapor is controlled by a computer controller to cause a selected pressure, a selected volume of vapor, and an optional aspiration of vapor condensate. Contemporaneous with tissue contact, the vapor undergoes a vapor-to-liquid phase transition which delivers large amount of energy to the targeted tissue. In one embodiment, the system is configured for volumetric removal of tissue by means of high velocity ejection of a vapor media from a first vapor port proximate to soft tissue wherein the vapor-to-liquid phase change of the media applies energy to the tissue. The system provides a second port coupled to a suction source that cooperates with the first vapor port to suction tissue debris from the targeted site.

10 Claims, 18 Drawing Sheets

Related U.S. Application Data continuation-in-part of application No. 10/681,628, filed on Oct. 8, 2003, now abandoned, and a continuation-in-part of application No. 10/346,877, filed on Jan. 18, 2003, now Pat. No. 6,911,028.

(60) Provisional application No. 60/615,900, filed on Oct. 5, 2004.

(51) Int. Cl.
*A61B 18/14* (2006.01)
*A61B 18/00* (2006.01)
*A61B 17/00* (2006.01)
*A61B 18/12* (2006.01)

(52) U.S. Cl.
CPC ..... *A61B18/042* (2013.01); *A61B 2017/00504* (2013.01); *A61B 2018/0041* (2013.01); *A61B 2018/00404* (2013.01); *A61B 2018/00541* (2013.01); *A61B 2018/00559* (2013.01); *A61B 2018/048* (2013.01); *A61B 2018/1213* (2013.01); *A61B 2218/002* (2013.01)

(56) References Cited

U.S. PATENT DOCUMENTS

| | | |
|---|---|---|
| 1,719,750 A | 9/1927 | Bridge et al. |
| 3,818,913 A | 6/1974 | Wallach |
| 3,880,168 A | 4/1975 | Berman |
| 3,930,505 A | 1/1976 | Wallach |
| 4,024,866 A | 5/1977 | Wallach |
| 4,083,077 A | 4/1978 | Knight et al. |
| 4,447,227 A | 5/1984 | Kotsanis |
| 4,672,962 A | 6/1987 | Hershenson |
| 4,682,596 A | 7/1987 | Bales et al. |
| 4,748,979 A | 6/1988 | Hershenson |
| 4,773,410 A | 9/1988 | Blackmer et al. |
| 4,793,352 A | 12/1988 | Eichenlaub |
| 4,872,920 A | 10/1989 | Flynn et al. |
| 4,898,574 A | 2/1990 | Uchiyama et al. |
| 4,915,113 A | 4/1990 | Holman |
| 4,950,266 A | 8/1990 | Sinofsky |
| 4,985,027 A | 1/1991 | Dressel |
| 5,006,119 A | 4/1991 | Acker et al. |
| 5,011,566 A | 4/1991 | Hoffman |
| 5,078,736 A | 1/1992 | Behl |
| 5,084,043 A | 1/1992 | Hertzmann et al. |
| 5,102,410 A | 4/1992 | Dressel |
| 5,112,328 A | 5/1992 | Taboada et al. |
| 5,122,138 A | 6/1992 | Manwaring |
| 5,158,536 A | 10/1992 | Sekins et al. |
| 5,162,374 A | 11/1992 | Mulieri et al. |
| 5,190,539 A | 3/1993 | Fletcher et al. |
| 5,217,459 A | 6/1993 | Kamerling |
| 5,217,465 A | 6/1993 | Steppe |
| 5,263,951 A | 11/1993 | Spears et al. |
| 5,277,696 A | 1/1994 | Hagen |
| 5,298,298 A | 3/1994 | Hoffman |
| 5,306,274 A | 4/1994 | Long |
| 5,318,014 A | 6/1994 | Carter |
| 5,331,947 A | 7/1994 | Shturman |
| 5,334,190 A | 8/1994 | Seiler |
| 5,344,397 A | 9/1994 | Heaven et al. |
| 5,348,551 A | 9/1994 | Spears et al. |
| 5,352,512 A | 10/1994 | Hoffman |
| 5,417,686 A | 5/1995 | Peterson et al. |
| 5,424,620 A | 6/1995 | Cheon et al. |
| 5,433,708 A | 7/1995 | Nichols et al. |
| 5,433,739 A | 7/1995 | Sluijter |
| 5,462,521 A | 10/1995 | Brucker et al. |
| 5,500,012 A | 3/1996 | Brucker et al. |
| 5,503,638 A | 4/1996 | Cooper et al. |
| 5,524,620 A | 6/1996 | Rosenschein |
| 5,529,076 A | 6/1996 | Schachar |
| 5,542,928 A | 8/1996 | Evans et al. |
| 5,549,628 A | 8/1996 | Cooper et al. |
| 5,554,172 A | 9/1996 | Horner et al. |
| 5,562,608 A | 10/1996 | Sekins et al. |
| 5,575,803 A | 11/1996 | Cooper et al. |
| 5,584,872 A | 12/1996 | LaFontaine et al. |
| 5,591,157 A | 1/1997 | Hennings et al. |
| 5,591,162 A | 1/1997 | Fletcher et al. |
| 5,616,120 A | 4/1997 | Andrew et al. |
| 5,620,440 A | 4/1997 | Heckele et al. |
| 5,669,907 A | 9/1997 | Platt, Jr. et al. |
| 5,681,282 A | 10/1997 | Eggers et al. |
| 5,683,366 A | 11/1997 | Eggers et al. |
| 5,695,507 A | 12/1997 | Auth et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,707,352 A | 1/1998 | Sekins et al. |
| 5,735,811 A | 4/1998 | Brisken |
| 5,741,247 A | 4/1998 | Rizoiu et al. |
| 5,741,248 A | 4/1998 | Stern et al. |
| 5,752,965 A | 5/1998 | Francis et al. |
| 5,755,753 A | 5/1998 | Knowlton |
| 5,782,914 A | 7/1998 | Schankereli |
| 5,785,521 A | 7/1998 | Rizoiu et al. |
| 5,800,482 A | 9/1998 | Pomeranz et al. |
| 5,810,764 A | 9/1998 | Eggers et al. |
| 5,824,703 A | 10/1998 | Clark, Jr. |
| 5,827,268 A | 10/1998 | Laufer |
| 5,836,896 A | 11/1998 | Rosenschein |
| 5,843,019 A | 12/1998 | Eggers et al. |
| 5,843,073 A | 12/1998 | Sinofsky |
| 5,871,469 A | 2/1999 | Eggers et al. |
| 5,879,329 A | 3/1999 | Ginsburg |
| 5,885,243 A | 3/1999 | Capetan et al. |
| 5,888,198 A | 3/1999 | Eggers et al. |
| 5,891,095 A | 4/1999 | Eggers et al. |
| 5,891,134 A | 4/1999 | Goble et al. |
| 5,913,856 A | 6/1999 | Chia et al. |
| 5,938,660 A | 8/1999 | Swartz et al. |
| 5,944,686 A | 8/1999 | Patterson et al. |
| 5,944,715 A | 8/1999 | Goble et al. |
| 5,957,919 A | 9/1999 | Laufer |
| 5,964,752 A | 10/1999 | Stone |
| 5,968,037 A | 10/1999 | Rizoiu |
| 5,980,504 A | 11/1999 | Sharkey et al. |
| 5,986,662 A | 11/1999 | Argiro et al. |
| 5,989,212 A | 11/1999 | Sussman et al. |
| 5,989,238 A | 11/1999 | Ginsburg |
| 5,989,249 A | 11/1999 | Kirwan |
| 5,989,445 A | 11/1999 | Wise et al. |
| 5,997,499 A | 12/1999 | Sussman et al. |
| 6,024,095 A | 2/2000 | Stanley, III |
| 6,024,733 A | 2/2000 | Eggers et al. |
| 6,027,501 A | 2/2000 | Goble et al. |
| 6,032,077 A | 2/2000 | Pomeranz |
| 6,032,674 A | 3/2000 | Eggers et al. |
| 6,047,700 A | 4/2000 | Eggers et al. |
| 6,053,909 A | 4/2000 | Shadduck |
| 6,056,746 A | 5/2000 | Goble et al. |
| 6,059,011 A | 5/2000 | Giolo |
| 6,063,079 A | 5/2000 | Hovda et al. |
| 6,063,081 A | 5/2000 | Mulier et al. |
| 6,066,134 A | 5/2000 | Eggers et al. |
| 6,066,139 A * | 5/2000 | Ryan et al. ............. 606/50 |
| 6,074,358 A | 6/2000 | Andrew et al. |
| 6,080,128 A | 6/2000 | Sussman et al. |
| 6,080,151 A | 6/2000 | Swartz et al. |
| 6,083,255 A | 7/2000 | Laufer et al. |
| 6,095,149 A | 8/2000 | Sharkey et al. |
| 6,099,251 A | 8/2000 | LaFleur |
| 6,102,046 A | 8/2000 | Weinstein et al. |
| 6,102,885 A | 8/2000 | Bass |
| 6,106,516 A | 8/2000 | Bmassengill |
| 6,110,162 A | 8/2000 | Sussman et al. |
| 6,113,722 A | 9/2000 | Hoffman et al. |
| 6,126,682 A | 10/2000 | Sharkey et al. |

(56) References Cited

U.S. PATENT DOCUMENTS

| | | | |
|---|---|---|---|
| 6,130,671 A | 10/2000 | Argiro | |
| 6,139,571 A * | 10/2000 | Fuller et al. | 607/105 |
| 6,149,620 A | 11/2000 | Baker et al. | |
| 6,156,036 A | 12/2000 | Sussman et al. | |
| 6,159,194 A | 12/2000 | Eggers et al. | |
| 6,162,232 A | 12/2000 | Shadduck | |
| 6,168,594 B1 | 1/2001 | LaFontaine et al. | |
| 6,174,308 B1 | 1/2001 | Goble et al. | |
| 6,179,805 B1 | 1/2001 | Sussman et al. | |
| 6,190,381 B1 | 2/2001 | Olsen et al. | |
| 6,194,066 B1 | 2/2001 | Hoffman | |
| 6,196,989 B1 | 3/2001 | Padget et al. | |
| 6,200,333 B1 | 3/2001 | Laufer | |
| 6,206,848 B1 | 3/2001 | Sussman et al. | |
| 6,210,404 B1 | 4/2001 | Shadduck | |
| 6,210,405 B1 | 4/2001 | Goble et al. | |
| 6,219,059 B1 | 4/2001 | Argiro | |
| 6,224,592 B1 | 5/2001 | Eggers et al. | |
| 6,231,567 B1 | 5/2001 | Rizoiu et al. | |
| 6,235,020 B1 | 5/2001 | Cheng et al. | |
| 6,238,391 B1 | 5/2001 | Olsen et al. | |
| 6,254,597 B1 | 7/2001 | Rizoiu et al. | |
| 6,261,286 B1 | 7/2001 | Goble et al. | |
| 6,261,311 B1 | 7/2001 | Sharkey et al. | |
| 6,264,650 B1 | 7/2001 | Hovda et al. | |
| 6,264,651 B1 | 7/2001 | Underwood et al. | |
| 6,264,654 B1 | 7/2001 | Swartz et al. | |
| 6,277,112 B1 | 8/2001 | Underwood et al. | |
| 6,283,910 B1 | 9/2001 | Bradshaw et al. | |
| 6,283,961 B1 | 9/2001 | Underwood et al. | |
| 6,283,989 B1 | 9/2001 | Laufer et al. | |
| 6,287,274 B1 | 9/2001 | Sussman et al. | |
| 6,290,715 B1 | 9/2001 | Sharkey et al. | |
| 6,296,636 B1 | 10/2001 | Cheng et al. | |
| 6,296,638 B1 | 10/2001 | Davidson et al. | |
| 6,299,633 B1 | 10/2001 | Laufer | |
| 6,300,150 B1 | 10/2001 | Venkatasubramanian | |
| 6,312,408 B1 | 11/2001 | Eggers et al. | |
| 6,312,474 B1 | 11/2001 | Francis et al. | |
| 6,315,755 B1 | 11/2001 | Sussman | |
| 6,319,222 B1 | 11/2001 | Andrew et al. | |
| 6,327,505 B1 | 12/2001 | Medhkour et al. | |
| 6,331,171 B1 | 12/2001 | Cohen | |
| 6,355,032 B1 | 3/2002 | Hovda et al. | |
| 6,375,635 B1 | 4/2002 | Moutafis et al. | |
| 6,379,350 B1 | 4/2002 | Sharkey et al. | |
| 6,391,025 B1 | 5/2002 | Weinstein et al. | |
| 6,394,949 B1 | 5/2002 | Crowley et al. | |
| 6,394,996 B1 | 5/2002 | Lawrence et al. | |
| 6,398,759 B1 | 6/2002 | Sussman et al. | |
| 6,398,775 B1 | 6/2002 | Perkins et al. | |
| 6,409,723 B1 | 6/2002 | Edwards | |
| 6,416,508 B1 | 7/2002 | Eggers et al. | |
| 6,458,231 B1 | 10/2002 | Wapner et al. | |
| 6,461,350 B1 | 10/2002 | Underwood et al. | |
| 6,464,694 B1 | 10/2002 | Massengil | |
| 6,464,695 B2 | 10/2002 | Hovda et al. | |
| 6,468,270 B1 | 10/2002 | Hovda et al. | |
| 6,468,274 B1 | 10/2002 | Alleyne et al. | |
| 6,468,313 B1 | 10/2002 | Claeson et al. | |
| 6,482,201 B1 | 11/2002 | Olsen et al. | |
| 6,482,202 B1 | 11/2002 | Goble et al. | |
| 6,488,673 B1 | 12/2002 | Laufer et al. | |
| 6,493,589 B1 | 12/2002 | Medhkour et al. | |
| 6,500,173 B2 | 12/2002 | Underwood et al. | |
| 6,508,816 B2 | 1/2003 | Shadduck | |
| 6,517,568 B1 | 2/2003 | Sharkey et al. | |
| 6,522,930 B1 | 2/2003 | Schaer et al. | |
| 6,527,761 B1 | 3/2003 | Soltesz et al. | |
| 6,527,766 B1 | 3/2003 | Bair | |
| 6,540,741 B1 | 4/2003 | Underwood et al. | |
| 6,544,211 B1 | 4/2003 | Andrew et al. | |
| 6,544,248 B1 | 4/2003 | Bass | |
| 6,547,810 B1 | 4/2003 | Sharkey et al. | |
| 6,558,379 B1 | 5/2003 | Batchelor et al. | |
| 6,575,929 B2 | 6/2003 | Sussman et al. | |
| 6,575,968 B1 | 6/2003 | Eggers et al. | |
| 6,579,270 B2 | 6/2003 | Sussman et al. | |
| 6,582,423 B1 | 6/2003 | Thapliyal et al. | |
| 6,585,639 B1 | 7/2003 | Kotmel et al. | |
| 6,588,613 B1 | 7/2003 | Pechenik et al. | |
| 6,589,201 B1 | 7/2003 | Sussman et al. | |
| 6,589,204 B1 | 7/2003 | Sussman et al. | |
| 6,592,594 B2 | 7/2003 | Rimbaugh et al. | |
| 6,595,990 B1 | 7/2003 | Weinstein et al. | |
| 6,599,311 B1 | 7/2003 | Biggs et al. | |
| 6,602,248 B1 | 8/2003 | Sharps et al. | |
| 6,605,087 B2 | 8/2003 | Swartz et al. | |
| 6,610,043 B1 | 8/2003 | Ingenito | |
| 6,620,130 B1 | 9/2003 | Ginsburg | |
| 6,620,155 B2 | 9/2003 | Underwood et al. | |
| 6,623,444 B2 | 9/2003 | Babaev | |
| 6,632,193 B1 | 10/2003 | Davison et al. | |
| 6,632,220 B1 | 10/2003 | Eggers et al. | |
| 6,634,363 B1 | 10/2003 | Danek et al. | |
| 6,648,847 B2 | 11/2003 | Sussman et al. | |
| 6,652,594 B2 | 11/2003 | Francis et al. | |
| 6,653,525 B2 | 11/2003 | Ingenito et al. | |
| 6,659,106 B1 | 12/2003 | Hovda et al. | |
| 6,669,685 B1 | 12/2003 | Rizoiu et al. | |
| 6,669,694 B2 | 12/2003 | Shadduck | |
| 6,676,628 B2 | 1/2004 | Sussman et al. | |
| 6,676,629 B2 | 1/2004 | Andrew et al. | |
| 6,679,264 B1 | 1/2004 | Deem et al. | |
| 6,679,879 B2 | 1/2004 | Shadduck | |
| 6,682,520 B2 | 1/2004 | Ingenito | |
| 6,682,543 B2 | 1/2004 | Barbut et al. | |
| 6,692,494 B1 | 2/2004 | Cooper et al. | |
| 6,695,839 B2 | 2/2004 | Sharkey et al. | |
| 6,699,212 B1 | 3/2004 | Kadziauskas et al. | |
| 6,699,244 B2 | 3/2004 | Carranza et al. | |
| 6,712,811 B2 | 3/2004 | Underwood et al. | |
| 6,712,812 B2 | 3/2004 | Roschak et al. | |
| 6,719,738 B2 | 4/2004 | Mehier | |
| 6,719,754 B2 | 4/2004 | Underwood et al. | |
| 6,723,064 B2 | 4/2004 | Babaev | |
| 6,726,684 B1 | 4/2004 | Woloszko et al. | |
| 6,726,708 B2 | 4/2004 | Lasheras | |
| 6,746,447 B2 | 6/2004 | Davison et al. | |
| 6,755,794 B2 | 6/2004 | Soukup | |
| 6,758,846 B2 | 7/2004 | Goble et al. | |
| 6,763,836 B2 | 7/2004 | Tasto et al. | |
| 6,764,487 B2 | 7/2004 | Mulier et al. | |
| 6,766,202 B2 | 7/2004 | Underwood et al. | |
| 6,770,070 B1 | 8/2004 | Balbierz | |
| 6,772,012 B2 | 8/2004 | Woloszko et al. | |
| 6,776,765 B2 | 8/2004 | Soukup et al. | |
| 6,780,180 B1 | 8/2004 | Goble et al. | |
| 6,805,130 B2 | 10/2004 | Tasto et al. | |
| 6,813,520 B2 | 11/2004 | Truckai et al. | |
| 6,832,996 B2 | 12/2004 | Woloszko et al. | |
| 6,837,884 B2 | 1/2005 | Woloszko | |
| 6,837,888 B2 | 1/2005 | Ciarrocca et al. | |
| 6,852,108 B2 | 2/2005 | Barry et al. | |
| 6,860,847 B2 | 3/2005 | Alferness et al. | |
| 6,860,868 B1 | 3/2005 | Sussman et al. | |
| 6,875,194 B2 | 4/2005 | MacKool | |
| 6,896,674 B1 | 5/2005 | Woloszko et al. | |
| 6,896,675 B2 | 5/2005 | Leung et al. | |
| 6,901,927 B2 | 6/2005 | Deem et al. | |
| 6,904,909 B2 | 6/2005 | Andreas et al. | |
| 6,907,881 B2 | 6/2005 | Suki et al. | |
| 6,911,028 B2 | 6/2005 | Shadduck | |
| 6,918,903 B2 | 7/2005 | Bass | |
| 6,921,385 B2 | 7/2005 | Clements et al. | |
| 6,929,640 B1 | 8/2005 | Underwood et al. | |
| 6,949,096 B2 | 9/2005 | Davison et al. | |
| 6,955,675 B2 | 10/2005 | Jain | |
| 6,960,182 B2 | 11/2005 | Moutafis et al. | |
| 6,962,584 B1 | 11/2005 | Stone et al. | |
| 6,972,014 B2 | 12/2005 | Eum et al. | |
| 6,978,174 B2 | 12/2005 | Gelfand et al. | |
| 6,986,769 B2 | 1/2006 | Nelson et al. | |
| 6,991,028 B2 | 1/2006 | Comeaux et al. | |

(56) References Cited

U.S. PATENT DOCUMENTS

| | | |
|---|---|---|
| 6,991,631 B2 | 1/2006 | Woloszko et al. |
| 7,022,088 B2 | 4/2006 | Keast et al. |
| 7,031,504 B1 | 4/2006 | Argiro et al. |
| 7,083,612 B2 | 8/2006 | Littrup et al. |
| 7,094,249 B1 | 8/2006 | Broome et al. |
| 7,128,748 B2 | 10/2006 | Mooradian et al. |
| 7,136,064 B2 | 11/2006 | Zuiderveld |
| 7,144,402 B2 | 12/2006 | Kuester, III |
| 7,144,588 B2 | 12/2006 | Oray et al. |
| 7,162,303 B2 | 1/2007 | Levin et al. |
| 7,192,400 B2 | 3/2007 | Campbell et al. |
| 7,233,820 B2 | 6/2007 | Gilboa |
| 7,235,070 B2 | 6/2007 | Vanney |
| 7,311,708 B2 | 12/2007 | McClurken |
| 7,335,195 B2 | 2/2008 | Mehier |
| 7,347,859 B2 | 3/2008 | Garabedian et al. |
| 7,524,315 B2 | 4/2009 | Blott et al. |
| 7,549,987 B2 | 6/2009 | Shadduck |
| 7,585,295 B2 | 9/2009 | Ben-Nun |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,674,259 B2 | 3/2010 | Shadduck |
| 7,717,948 B2 | 5/2010 | Demarais et al. |
| 7,756,583 B2 | 7/2010 | Demarais et al. |
| 7,815,616 B2 | 10/2010 | Boehringer et al. |
| 7,815,646 B2 | 10/2010 | Hart |
| 7,853,333 B2 | 12/2010 | Demarais |
| 7,873,417 B2 | 1/2011 | Demarais et al. |
| 7,892,229 B2 | 2/2011 | Shadduck et al. |
| 7,937,143 B2 | 5/2011 | Demarais et al. |
| 7,993,323 B2 | 8/2011 | Barry et al. |
| 8,016,823 B2 | 9/2011 | Shadduck |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,187,269 B2 | 5/2012 | Shadduck et al. |
| 8,192,424 B2 | 6/2012 | Woloszko |
| 8,313,485 B2 | 11/2012 | Shadduck |
| 8,444,636 B2 | 5/2013 | Shadduck et al. |
| 8,574,226 B2 | 11/2013 | Shadduck |
| 8,579,888 B2 | 11/2013 | Hoey et al. |
| 8,579,892 B2 | 11/2013 | Hoey et al. |
| 8,579,893 B2 | 11/2013 | Hoey |
| 2001/0020167 A1 | 9/2001 | Woloszko et al. |
| 2001/0029370 A1 | 10/2001 | Hodva et al. |
| 2001/0037106 A1 | 11/2001 | Shadduck |
| 2002/0049438 A1 | 4/2002 | Sharkey et al. |
| 2002/0077516 A1 | 6/2002 | Flanigan |
| 2002/0078956 A1 | 6/2002 | Sharpe et al. |
| 2002/0082667 A1 | 6/2002 | Shadduck |
| 2002/0095152 A1 | 7/2002 | Ciarrocca et al. |
| 2002/0111386 A1 | 8/2002 | Sekins et al. |
| 2002/0128638 A1 | 9/2002 | Chauvet et al. |
| 2002/0133147 A1 | 9/2002 | Marchitto et al. |
| 2002/0161326 A1 | 10/2002 | Sussman et al. |
| 2002/0177846 A1* | 11/2002 | Mulier et al. .............. 606/27 |
| 2002/0193789 A1 | 12/2002 | Underwood et al. |
| 2003/0028189 A1 | 2/2003 | Woloszko et al. |
| 2003/0040742 A1 | 2/2003 | Underwood et al. |
| 2003/0097126 A1 | 5/2003 | Woloszko et al. |
| 2003/0097129 A1 | 5/2003 | Davison et al. |
| 2003/0099279 A1 | 5/2003 | Venkatasubramanian et al. |
| 2003/0109869 A1 | 6/2003 | Shadduck |
| 2003/0130655 A1 | 7/2003 | Woloszko et al. |
| 2003/0130738 A1 | 7/2003 | Hovda et al. |
| 2003/0144654 A1 | 7/2003 | Hilal |
| 2003/0158545 A1 | 8/2003 | Hovda et al. |
| 2003/0163178 A1 | 8/2003 | Davison et al. |
| 2003/0181922 A1 | 9/2003 | Alferness |
| 2003/0212394 A1 | 11/2003 | Pearson et al. |
| 2003/0212395 A1 | 11/2003 | Woloszko et al. |
| 2003/0225364 A1 | 12/2003 | Kraft et al. |
| 2004/0024398 A1 | 2/2004 | Hovda et al. |
| 2004/0024399 A1 | 2/2004 | Sharps et al. |
| 2004/0031494 A1 | 2/2004 | Danek et al. |
| 2004/0038868 A1 | 2/2004 | Ingenito |
| 2004/0047855 A1 | 3/2004 | Ingenito |
| 2004/0049180 A1 | 3/2004 | Sharps et al. |
| 2004/0054366 A1 | 3/2004 | Davison et al. |
| 2004/0055606 A1 | 3/2004 | Hendricksen et al. |
| 2004/0068256 A1 | 4/2004 | Rizoiu et al. |
| 2004/0068306 A1 | 4/2004 | Shadduck |
| 2004/0087937 A1 | 5/2004 | Eggers et al. |
| 2004/0116922 A1 | 6/2004 | Hovda et al. |
| 2004/0193150 A1 | 9/2004 | Sharkey et al. |
| 2004/0199226 A1 | 10/2004 | Shadduck |
| 2004/0230190 A1 | 11/2004 | Dahla et al. |
| 2004/0254532 A1 | 12/2004 | Mehier |
| 2005/0004634 A1 | 1/2005 | Ricart et al. |
| 2005/0010205 A1 | 1/2005 | Hovda et al. |
| 2005/0070894 A1 | 3/2005 | McClurken |
| 2005/0119650 A1 | 6/2005 | Sanders et al. |
| 2005/0166925 A1 | 8/2005 | Wilson et al. |
| 2005/0171582 A1 | 8/2005 | Matlock |
| 2005/0187543 A1 | 8/2005 | Underwood et al. |
| 2005/0215991 A1 | 9/2005 | Altman et al. |
| 2005/0222485 A1 | 10/2005 | Shaw et al. |
| 2005/0228423 A1 | 10/2005 | Khashayar et al. |
| 2005/0228424 A1 | 10/2005 | Khashayar et al. |
| 2005/0240171 A1 | 10/2005 | Forrest |
| 2005/0267467 A1 | 12/2005 | Paul et al. |
| 2005/0283143 A1 | 12/2005 | Rizoiu |
| 2006/0004400 A1 | 1/2006 | McGurk et al. |
| 2006/0047291 A1 | 3/2006 | Barry |
| 2006/0085054 A1 | 4/2006 | Zikorus et al. |
| 2006/0100619 A1 | 5/2006 | McClurken et al. |
| 2006/0130830 A1 | 6/2006 | Barry |
| 2006/0135955 A1 | 6/2006 | Shadduck |
| 2006/0142783 A1 | 6/2006 | Lewis et al. |
| 2006/0161233 A1 | 7/2006 | Barry et al. |
| 2006/0200076 A1 | 9/2006 | Gonzalez et al. |
| 2006/0206150 A1 | 9/2006 | Demarais et al. |
| 2006/0224154 A1 | 10/2006 | Shadduck et al. |
| 2006/0271111 A1 | 11/2006 | Demarais et al. |
| 2007/0032785 A1 | 2/2007 | Diederich et al. |
| 2007/0036417 A1 | 2/2007 | Argiro et al. |
| 2007/0091087 A1 | 4/2007 | Zuiderveld |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0265687 A1 | 11/2007 | Deem et al. |
| 2008/0033493 A1 | 2/2008 | Deckman et al. |
| 2008/0097429 A1 | 4/2008 | McClurken |
| 2008/0103566 A1 | 5/2008 | Mehier |
| 2008/0110457 A1 | 5/2008 | Barry et al. |
| 2008/0114297 A1 | 5/2008 | Barry et al. |
| 2008/0125747 A1 | 5/2008 | Prokop |
| 2008/0132826 A1 | 6/2008 | Shadduck et al. |
| 2008/0213331 A1 | 9/2008 | Gelfand et al. |
| 2008/0255642 A1 | 10/2008 | Zarins et al. |
| 2009/0036948 A1 | 2/2009 | Levin et al. |
| 2009/0054871 A1 | 2/2009 | Sharkey et al. |
| 2009/0062873 A1 | 3/2009 | Wu et al. |
| 2009/0076409 A1 | 3/2009 | Wu et al. |
| 2009/0105702 A1 | 4/2009 | Shadduck |
| 2009/0105703 A1 | 4/2009 | Shadduck |
| 2009/0125009 A1 | 5/2009 | Zikorus et al. |
| 2009/0149846 A1 | 6/2009 | Hoey et al. |
| 2009/0216220 A1 | 8/2009 | Hoey et al. |
| 2009/0306640 A1 | 12/2009 | Glaze et al. |
| 2009/0312753 A1 | 12/2009 | Shadduck |
| 2010/0076416 A1 | 3/2010 | Hoey et al. |
| 2010/0094270 A1 | 4/2010 | Sharma |
| 2010/0114083 A1 | 5/2010 | Sharma |
| 2010/0137860 A1 | 6/2010 | Demarais et al. |
| 2010/0137952 A1 | 6/2010 | Demarais et al. |

(56) References Cited

U.S. PATENT DOCUMENTS

| | | |
|---|---|---|
| 2010/0160905 A1 | 6/2010 | Shadduck |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0179528 A1 | 7/2010 | Shadduck et al. |
| 2010/0185189 A1 | 7/2010 | Hoey |
| 2010/0191112 A1 | 7/2010 | Demarais et al. |
| 2010/0204688 A1 | 8/2010 | Hoey et al. |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0262133 A1 | 10/2010 | Hoey et al. |
| 2010/0268307 A1 | 10/2010 | Demarais et al. |
| 2011/0060324 A1 | 3/2011 | Wu et al. |
| 2011/0077628 A1 | 3/2011 | Hoey et al. |
| 2011/0112400 A1 | 5/2011 | Emery et al. |
| 2011/0118717 A1 | 5/2011 | Shadduck |
| 2011/0160648 A1 | 6/2011 | Hoey |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0208096 A1 | 8/2011 | Demarais et al. |
| 2011/0257564 A1 | 10/2011 | Demarais et al. |
| 2011/0264011 A1 | 10/2011 | Wu et al. |
| 2011/0264075 A1 | 10/2011 | Leung et al. |
| 2011/0264090 A1 | 10/2011 | Shadduck et al. |
| 2012/0065632 A1 | 3/2012 | Shadduck |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0116383 A1 | 5/2012 | Mauch et al. |
| 2012/0116486 A1 | 5/2012 | Naga et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130458 A1 | 5/2012 | Ryba et al. |
| 2012/0136344 A1 | 5/2012 | Buckley et al. |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0150267 A1 | 6/2012 | Buckley et al. |
| 2012/0158104 A1 | 6/2012 | Huynh et al. |
| 2012/0172837 A1 | 7/2012 | Demarais et al. |
| 2012/0197198 A1 | 8/2012 | Demarais et al. |
| 2012/0197252 A1 | 8/2012 | Deem et al. |
| 2012/0259271 A1 | 10/2012 | Shadduck et al. |
| 2013/0116683 A1 | 5/2013 | Shadduck et al. |
| 2013/0237978 A1 | 9/2013 | Shadduck et al. |
| 2014/0018890 A1 | 1/2014 | Hoey et al. |
| 2014/0025057 A1 | 1/2014 | Hoey et al. |
| 2014/0031805 A1 | 1/2014 | Shadduck |

FOREIGN PATENT DOCUMENTS

| | | |
|---|---|---|
| WO | WO 02/069821 | 9/2002 |
| WO | WO 03/070302 | 8/2003 |
| WO | WO 03/086498 | 10/2003 |
| WO | WO 2005/025635 | 3/2005 |
| WO | WO 2005/102175 | 11/2005 |
| WO | WO 2006/003665 | 1/2006 |
| WO | WO 2006/055695 | 5/2006 |
| WO | WO 2009/009398 | 1/2009 |

OTHER PUBLICATIONS

Fishman et al., "A randomized trial comparing lung-volume-reduction surgery with medical therapy for severe emphysema," *N Engl J Med*, vol. 348, No. 21, pp. 2059-2073, May 22, 2003.

Homasson, et al., "Bronchoscopic cryotherapy for airway strictures caused by tumors," *Chest*, vol. 90, No. 2, pp. 159-164, Aug. 1986.

Li, K., "Efficient optimal net surface detection for image segmentation—from theory to practice," M.Sc. Thesis, The University of Iowa, 2003.

Marasso, et al., "Cryosurgery in bronchoscopic treatment of tracheobronchial stenosis," *Chest*, vol. 103, No. 2, pp. 472-474, Feb. 1993.

Marasso, et al., "Radiefrequency resection of bronchial tumours in combination with cryotherapy: evaluation of a new technique," *Thorax*, vol. 53, pp. 106-109, 1998.

Mathur et al., "Fiberoptic bronchoscopic cryotherapy in the management of tracheobronchial obstruction," *Chest*, vol. 110, No. 3, pp. 718-723, Sep. 1996.

Morice et al. "Endobtinchial argon plasma coagulation for treatment of hemotysis and neoplastic airway obstruction," *Chest*, vol. 119, No. 3, pp. 781-787, Mar. 2001.

Moulding et al., "Preliminary studies for achieving transcervical oviduct occlusion by hot water or low-pressure steam," *Advancesin Planned Parenthood*, vol. 12, No. 2; pp. 79-85, 1977.

Quin, J., "Use of neodymium yttrium aluminum garnet laser in long-term palliation of airway obstruction," *Connecticut Medicine*, vol. 59, No. 7, pp. 407-412, Jul. 1995.

Sutedja, et al., "Bronchoscopic treatment of lung tumors," *Elsevier, Lung Cancer*, 11, pp. 1-17, 1994.

Tschirren et al.; "Intrathoracic airway trees: segmentation and airway morphology analysis from low-dose CT scans;" *IEEE Trans. Med. Imaging*, vol. 24, No. 12; pp. 1529-1539, Dec. 2005.

Tschirren, J., "Segmentation, anatomical labeling, branchpoint matching, and quantitative analysis of human airway trees in volumetric CT images," Ph.D. Thesis, The University of Iowa, 231 pages, Aug. 2003.

Tschirren, J., "Segmentation, anatomical labeling, branchpoint matching, and quantitative analysis of human airway trees in volumetric CT images," Slides from Ph.D. defense, University of Iowa, 130 pages, Aug. 2003.

Unger, M. et al. "Monolithic Microfabncated Valves and Pumps by Multilayer Soft Lithography," *Science*, vol. 288, pp. 113-116, Apr. 7, 2000, accessed at http://web.mit.edu/thorsen/www/113.pdf.

Xia, Y. et al. "Soft Lithography," *Annu. Rev. Mater. Sci.*, vol. 28, pp. 153-184, 1998, accessed at http://www.bwfoundry.com.xia.pdf.

\* cited by examiner

METHOD FOR PERFORMING LUNG VOLUME REDUCTION

CROSS-REFERENCE TO RELATED APPLICATIONS

This application is a continuation of U.S. patent application Ser. No. 12/255,394 filed Oct. 21, 2008, now U.S. Pat. No. 8,313,485 issued Nov. 20, 2012, which is a continuation of U.S. patent application Ser. No. 11/244,329 filed Oct. 5, 2005, now U.S. Pat. No. 8,016,823 issued Sep. 13, 2011, which claims priority to U.S. Provisional Patent Application No. 60/615,900 filed Oct. 5, 2004 and is a continuation-in-part of U.S. patent application Ser. No. 10/346,877 filed Jan. 18, 2003, now U.S. Pat. No. 6,911,028 issued Jun. 28, 2005, and U.S. patent application Ser. No. 11/244,329 filed Oct. 5, 2005, now U.S. Pat. No. 8,016,823 is also a continuation-in-part of U.S. patent application Ser. No. 10/681,628 filed Oct. 7, 2003, now U.S. Pat. No. 7,674,259 issued Mar. 9, 2010, the contents of which are incorporated herein by reference in their entirety.

BACKGROUND OF THE INVENTION

This invention relates to surgical instruments for applying energy to tissue, and more particularly relates to a system for volumetric removal of tissue by means of high velocity ejection of a vapor media from a first vapor port proximate to soft tissue wherein the vapor-to-liquid phase change of the media applies energy to the tissue. Contemporaneously, the system provides a second port coupled to a suction source that cooperates with the first vapor port to suction tissue debris from the targeted site.

Various types of radiofrequency (Rf) and laser surgical instruments have been developed for delivering thermal energy to tissue, for example to ablate tissue, to cause hemostasis, to weld tissue or to cause a thermoplastic remodeling of tissue. While such prior art forms of energy delivery are suitable for some applications. Rf and laser energy typically cannot cause highly "controlled" and "localized" thermal effects that are desirable in microsurgeries or other precision surgeries. In general, the non-linear or nonuniform characteristics of tissue affect, both laser and Rf energy distributions in tissue.

What is needed for many surgical procedures is an instrument and technique that can controllably deliver energy to tissue for volumetric tissue removal or tissue cutting without the possibility of desiccation or charring of adjacent tissues, and without collateral thermal damage.

BRIEF SUMMARY OF THE INVENTION

The present invention is adapted to provide improved methods of controlled energy delivery to localized tissue volumes, for example for volumetric tissue removal or thermoplastic remodeling of tissue.

In general, the thermally-mediated treatment method comprises causing a vapor-to-liquid phase state change in a selected media at a targeted tissue site thereby applying thermal energy substantially equal to the heat of vaporization of the selected media to said tissue site. The thermally-mediated therapy can be delivered to tissue by such vapor-to-liquid phase transitions, or "internal energy" releases, about the working surfaces of several types of instruments for endoluminal treatments or for soft tissue thermotherapies. FIGS. 1A and 1B illustrate the phenomena of phase transitional releases of internal energies. Such internal energy involves energy on the molecular and atomic scale-and in polyatomic gases is directly related to intermolecular attractive forces, as well as rotational and vibration kinetic energy. In other words, the method of the invention exploits the phenomenon of internal energy transitions between gaseous and liquid phases that involve very large amounts of energy compared to specific heat.

It has been found that the controlled application of internal energies in an introduced media-tissue interaction solves many of the vexing problems associated with energy-tissue interactions in Rf, laser and ultrasound modalities. The apparatus of the invention provides a fluid-carrying chamber in the interior of the device or working end. A source provides liquid media to the interior chamber wherein energy is applied to instantly vaporize the media. In the process of the liquid-to-vapor phase transition of a saline media in the interior of the working end, large amounts of energy are added to overcome the cohesive forces between molecules in the liquid, and an additional amount of energy is requires to expand the liquid 1000+ percent (P∆D) into a resulting vapor phase (see FIG. 1A). Conversely, in the vapor-to-liquid transition, such energy will be released at the phase transitions at the targeted tissue interface. That is, the heat of vaporization is released in tissue when the media transitioning from gaseous phase to liquid phase wherein the random, disordered motion of molecules in the vapor regain cohesion to convert to a liquid media. This release of energy (defined as the capacity for doing work) relating to intermolecular attractive forces is transformed into therapeutic heat for a thermotherapy within a targeted body structure. Heat flow and work are both was of transferring energy.

In FIG. 1A, the simplified visualization of internal energy is useful for understanding phase transition phenomena that involve internal energy transitions between liquid and vapor phases. If heat were added at a constant rate in FIG. 1A (graphically represented as 5 calories/gin blocks) to elevate the temperature of water through its phase change to a vapor phase, the additional energy required to achieve the phase change (latent heat of vaporization) is represented by the large number of 110+ blocks of energy at 100° C. in FIG. 1A. Still referring to FIG. 1A, it can be easily understood that all other prior art ablation modalities—Rf, laser, microwave and ultrasound—create energy densities by simply ramping up calories/gm as indicated by the temperature range from 37° C. through 100° C. as in FIG. 1A. The prior art modalities make no use of the phenomenon of phase transition energies as depicted in FIG. 1A.

FIG. 1B graphically represents a block diagram relating to energy delivery aspects of the present invention. The system provides for insulative containment of an initial primary energy-media within an interior chamber of an instrument's working end. The initial, ascendant energy-media interaction delivers energy sufficient to achieve the heat of vaporization of a selected liquid media such as saline within an interior of the instrument body. This aspect of the technology requires an inventive energy source and controller-since energy application from the source to the selected, media (Rf, laser, microwave etc.) must be modulated between very large energy densities to initially surpass the latent heat of vaporization of the media within milliseconds, and possible subsequent lesser energy densities for maintaining the media in its vapor phase. Additionally, the energy delivery system is coupled to a pressure control system for replenishing the selected liquid phase media at the required rate-and optionally for controlling propagation velocity of the vapor phase media from the working end surface of the instrument. In use, the method of the invention comprises the controlled deposition of a large amount of energy-the heat of vaporization as in FIG. 1A—when the vapor-to-liquid phase transition is controlled at the vapor media-tissue interface. The vapor-to-liquid phase transition deposits about 580 cal/gram within the targeted tissue site to perform the thermal ablation.

In one embodiment, the system is configured for ablation and extraction of soft tissue, for example in treating a disc. The flow of vapor is controlled by a computer controller to cause a selected pressure, a selected volume of vapor to be ejected from a working end port. Contemporaneous with tissue contact, the vapor undergoes a vapor-to-liquid phase transition which delivers large amount of energy to the targeted tissue to obliterate or ablate the tissue. In one embodiment, the system causes volumetric removal of tissue by high velocity ejection of the vapor media from a first vapor port. The system provides a second port coupled to a suction source that cooperates with the first vapor port to suction tissue debris from the targeted site.

In another embodiment, the invention comprises a flexible micro-catheter device or other member for endoluminal introduction that carries a thermal energy emitter, for example first and second electrodes coupled to an electrical source, within at least one interior bore of the device's working end. In one embodiment, electrical discharges between opposing polarity electrodes are adapted to vaporize, cavitate and expand a fluid media that inflows into and though the interior bore. The working end is adapted for related methods of use in Type "C" embodiments. The Type "C" embodiment is designed to deliver energy to endoluminal media in the form of controlled therapeutic heat, without ohmic (resistive) heating of tissue as in practiced in prior art Rf devices.

In a Type "C" system corresponding to the invention, electrical energy is delivered to interior lumen of the working end that interfaces with pressurized fluid media inflows. In this embodiment, the working end is optimized for therapeutically heating the vessel walls to shrink, occlude or seal the lumen. One use of the Type "C" system is for closure of blood vessels to treat varicose veins. The working end causes controlled thermal effects in the vessel walls by means of superheated vapor that is propagated from the working surface. Advantageously, the peak temperatures cannot exceed about 100° C. which will prevent damage to nerves that extend along targeted vessels. Such nerves can easily be damaged if Rf energy and ohmic heating are used to obliterate blood vessels to treat varicose veins.

The Type "C" system and its method of use also can be used to apply therapeutic heat to vessel walls to treat chronic vascular insufficiency (CVI) or to shrink arterial vascular malformations (AVM) and aneurysms. The Type "C" system and method also can be used to apply therapeutic heat to any duct, cavity, lumen, septae or the like in the body to shrink, collapse or damage the anatomic walls or to fuse together and seal endothelial layers thereof.

Additional advantages of the invention will be apparent from the following description, the accompanying drawings and the appended claims.

BRIEF DESCRIPTION OF THE SEVERAL VIEWS OF THE DRAWINGS

FIG. 5 illustrating the pressurized delivery of a liquid media to an interior channel, and FIG. 6 depicting an electrical discharge that causes a liquid-to-gas phase change as well as the ejection of the vapor media into the targeted tissue to thermally seal engaged tissue.

DETAILED DESCRIPTION OF THE INVENTION

1. Type "A" Thermotherapy Instrument

Figure 1A:
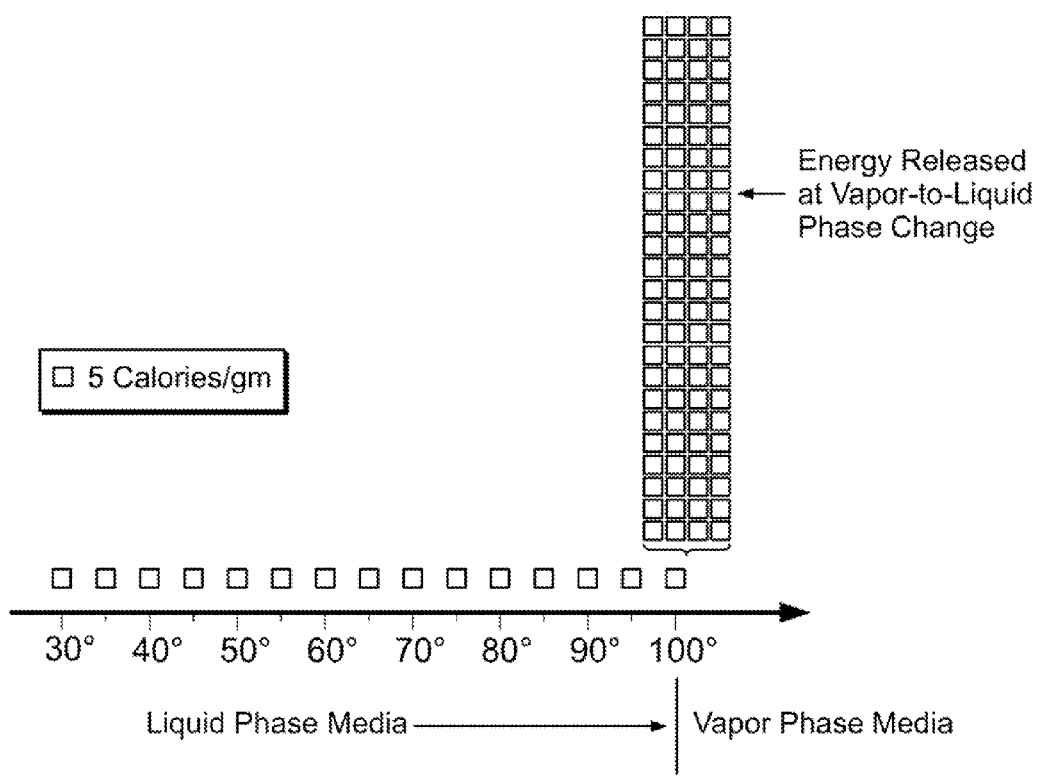
FIG. 1A is a graphical depiction of the quantity of energy needed to achieve the heat of vaporization of water.
Figure 1B:
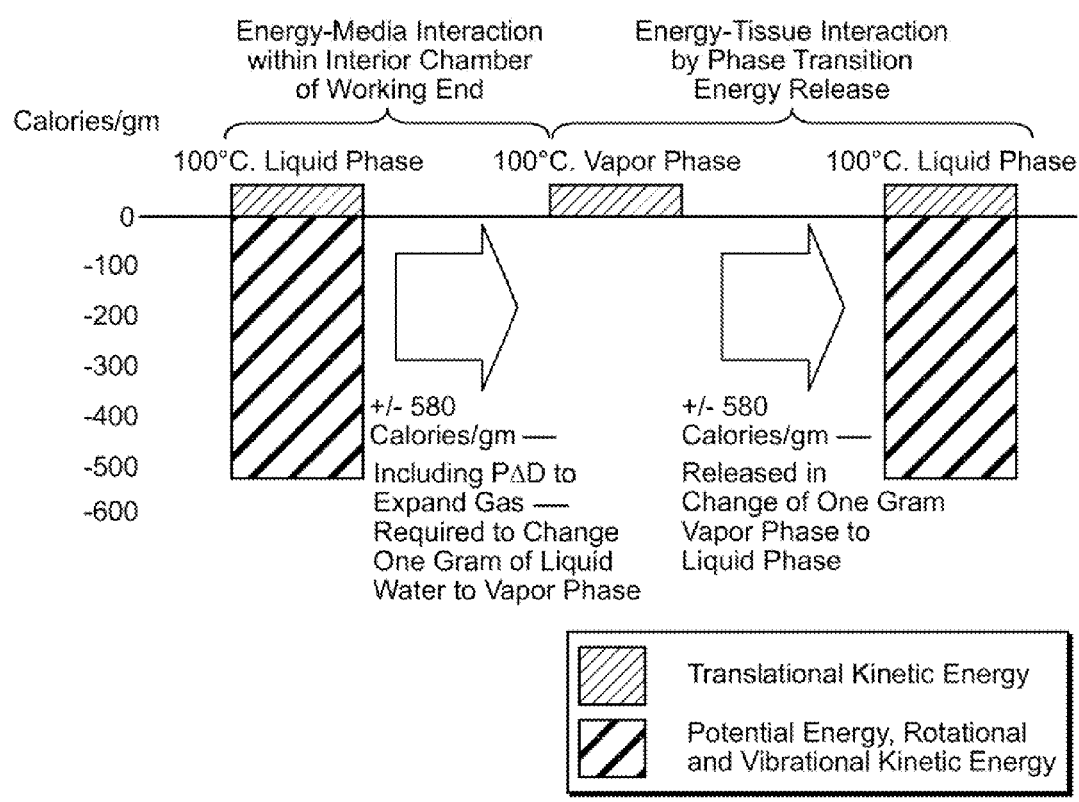
FIG. 1B is a diagram of phase change energy release that underlies one method of the invention.
Figure 2A:
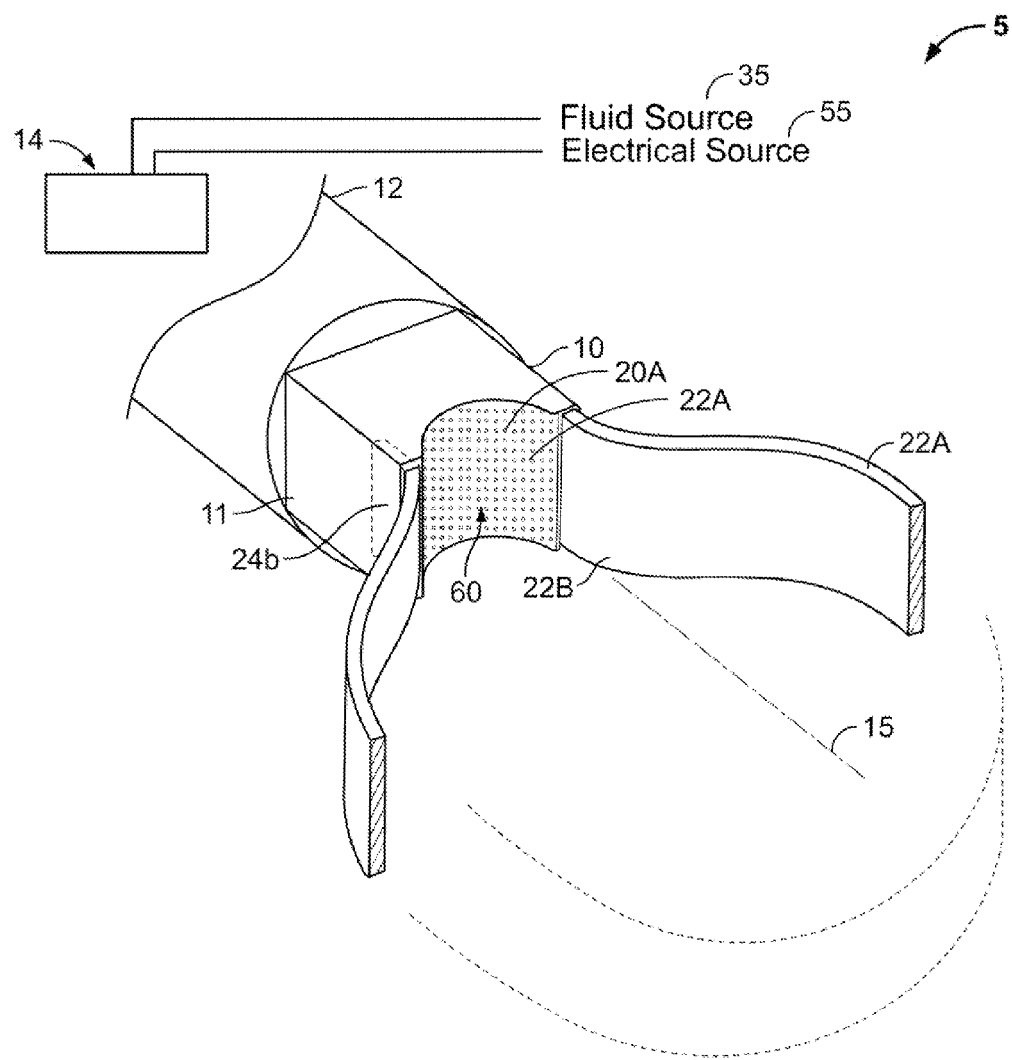
FIG. 2A is a perspective view of the working end of an exemplary Type "A" probe of the present invention with an openable-closeable tissue engaging structure in a first open position.
Figure 2B:
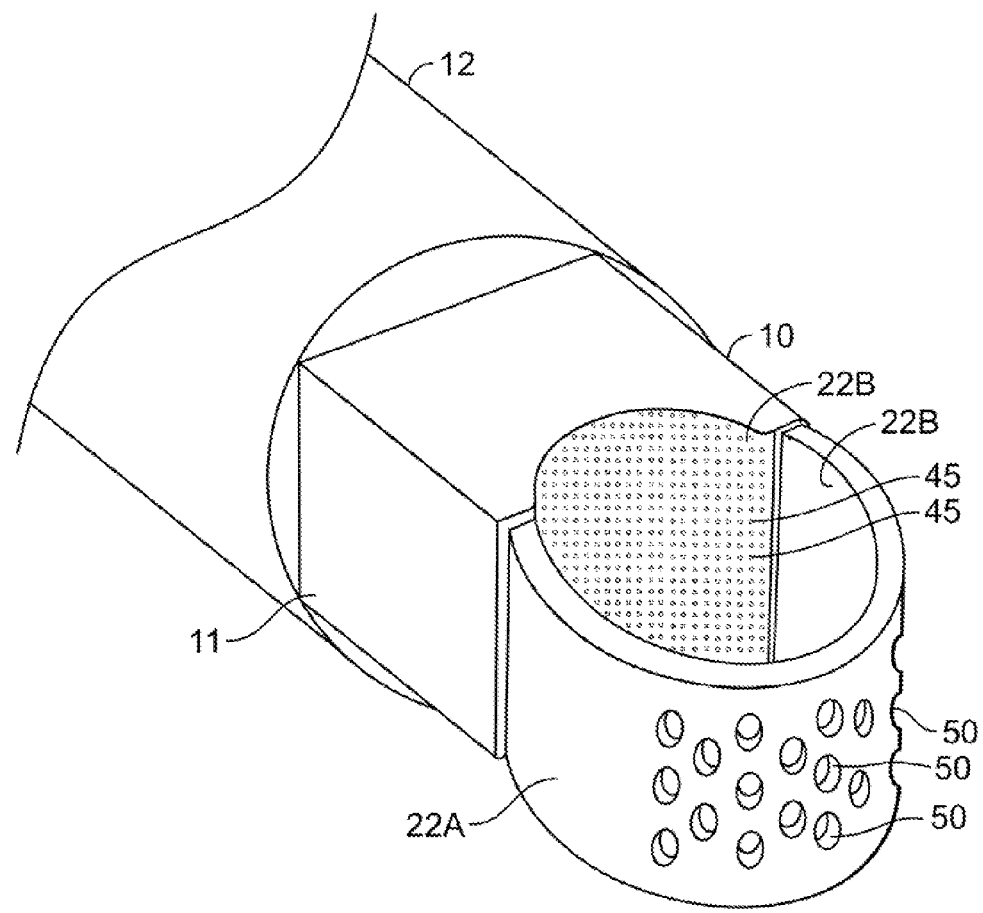
FIG. 2B is a perspective view similar to FIG. 2A probe of the present invention in a second closed position.
Figure 3:
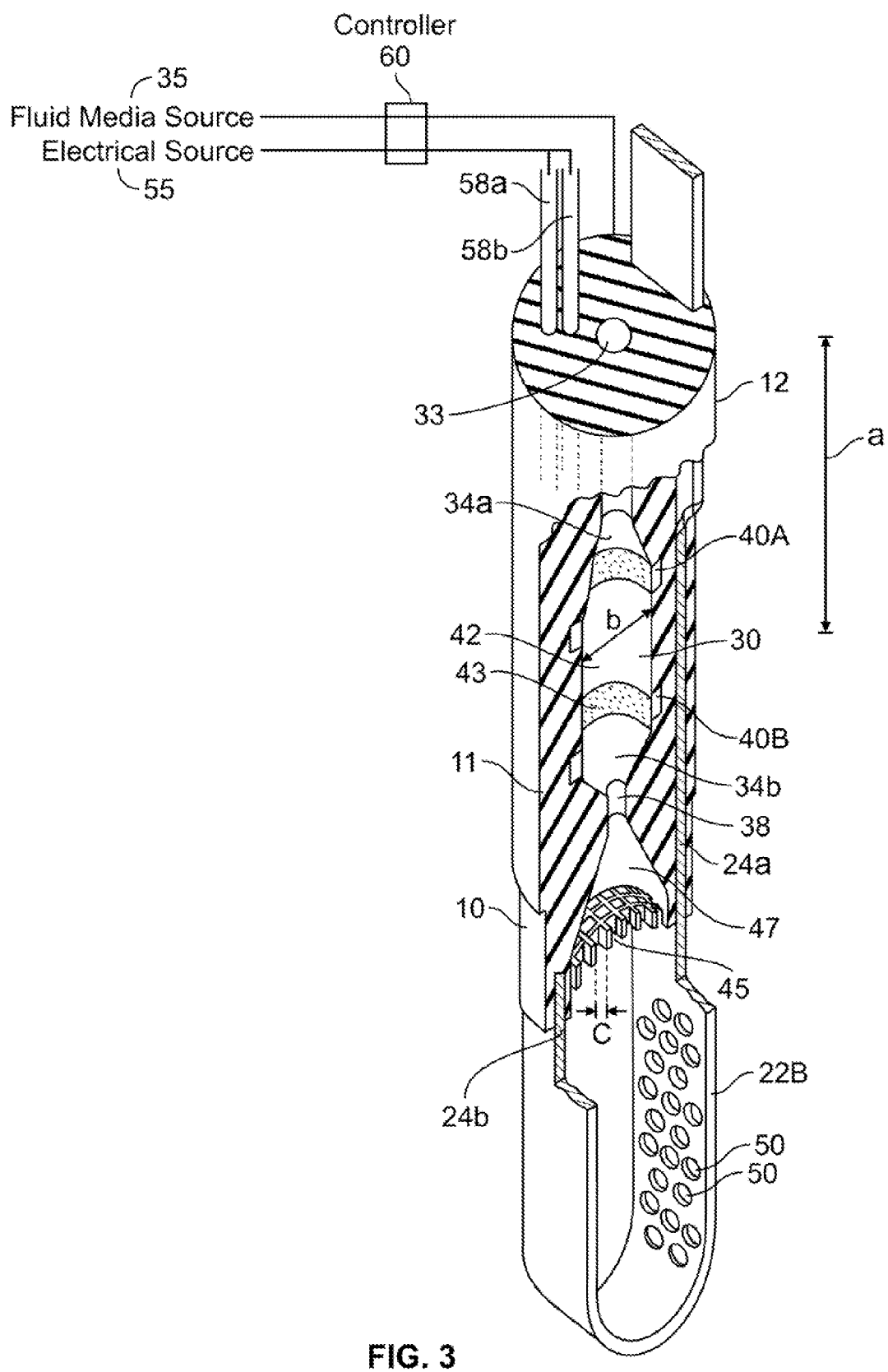
FIG. 3 is a cut-away view of the working end of FIGS. 2A-2B.

Referring to FIGS. 2A, 2B and 3, the working end 10 of a Type "A" system 5 of the present invention is shown that is adapted for endoscopic procedures in which a tissue volume T targeted for treatment (a thermoplasty) can be captured by a loop structure. The working end 10 comprises a body 11 of insulator material (see FIG. 3) coupled to the distal end of introducer member 12 extending, along axis 15. In this exemplary embodiment, the working end 10 has a generally cylindrical cross-section and is made of any suitable material such as plastic, ceramic, glass, metal or a combination thereof. The working end 10 is substantially small in diameter (e.g., 2 mm to 5 mm) and in this embodiment is coupled to an elongate flexible introducer member 12 to cooperate with a working channel in an endoscope. Alternatively, the working end 10 may be coupled to a rigid shaft member having a suitable 1 mm to 5 mm or larger diameter to cooperate with a trocar sleeve for use in endoscopic or microsurgical procedures. A proximal handle portion 14 of the instrument indicated by the block diagram of FIG. 2A carries the various actuator mechanisms known in the art for actuating components of the instrument.

In FIGS. 2A, 2B and 3, it can be seen that the working end 10 carries an openable and closeable structure for capturing tissue between a first tissue-engaging surface 20A and a second tissue-engaging surface 20B. In this exemplary embodiment, the working end 10 and first tissue-engaging surface 20A comprises a non-moving, component indicated at 22A that is defined by the exposed distal end of body 11 of working end 10. The second tissue-engaging surface 20B is carried in a moving component that comprises a flexible loop structure indicated at 22B.

The second moving component or flexible loop 22B is actuatable by a slidable portion 24a of the loop that extends through a slot 25 in the working end to an actuator in the handle portion 14 as is known in the art (see FIG. 3). The other end 24b of the loop structure 22B is fixed in body 11. While such an in-line (or axial) flexible slidable member is preferred as the tissue-capturing mechanism for a small diameter flexible catheter-type instrument, it should be appreciated that any openable and closable jaw structure known in the art falls within the scope of the invention, including forms of paired jaws with cam-surface actuation or conventional pin-type hinges and actuator mechanisms. FIG. 2A illustrates the first and second tissue-engaging surfaces 20A and 20B in a first spaced apart or open position. FIG. 2B shows the first and second surfaces 20A and 20B moved toward a second closed position.

Now turning to the fluid-to-gas energy delivery means of the invention, referring to FIG. 3, it can be seen that the insulated or non-conductive body 11 of working end 10 carries an interior chamber indicated at 30 communicating with lumen 33 that are together adapted for delivery and transient confinement of a fluid media M that flows into chamber 30. The chamber 30 communicates via lumen 33 with a fluid media source 35 that may be remote from the device, or a thud reservoir (coupled to a remote pressure source) carried within introducer 12 or carried within a handle portion 14. The term fluid or flowable media source 35 is defined to include a positive pressure inflow system which preferably is any suitable high pressure pump means known in the art. The fluid delivery lumen 33 transitions to chamber 30 at proximal end portion 34a thereof. The distal end portion 34b of chamber 30 has a reduced cross-section that functions to direct vapor media through a small outlet or nozzle indicated at 38.

Of particular interest, still referring to FIG. 3, paired spaced apart electrode elements 40A and 40B are exposed in surface 42 of interior fluid confinement chamber 30. In this exemplary embodiment, the electrode elements 40A and 40B comprise circumferential exposed surfaces of a conductive material positioned at opposing proximal and distal ends of interior chamber 30, but other arrangements are possible. The invention can utilize any suitable configuration of spaced apart electrodes (e.g., such as concentric electrode surfaces, intertwined helical electrode suffices, adjustable spaced apart surfaces, or porous electrodes) about at least one confinement chamber 30 or lumen portion of the system. Alternatively, each electrode can comprise one or more projecting elements that project into the chamber. The exemplary embodiment of FIG. 3 shows an elongate chamber having an axial dimension indicated at A and diameter or cross-section indicated at B. The axial dimension may range from about 0.1 mm to 20.0 mm and may be singular or plural as described below. The diameter B may range from micron dimensions (e.g., 0.5 μm) for miniaturized instruments to a larger dimension (e.g., 5.0 mm) for larger instruments for causing the thermally induced liquid-to-vapor transformation required to enable the novel phase change energy-tissue interaction of the invention. The electrodes are orally suitable material such as stainless steel, aluminum, nickel titanium, platinum, gold, or copper. Each electrode surface preferably has a toothed surface texture indicated at 43 that includes hatching, projecting elements or surface asperities for better delivering high energy densities in the fluid proximate to the electrode. The electrical current to the working end 10 may be switched on and off by a foot pedal or any other suitable means such as a switch in handle 14.

FIG. 3 further shows that a preferred shape is formed into the tissue-engaging surface 20A to better perform the method of fusing tissue. As can be seen in FIGS. 2B and 3, the first tissue-engaging surface 20A is generally concave so as to be adapted to receive a greater tissue volume in the central portion of surface 20A. The second tissue-engaging surface 20B is flexible and naturally will be concave in the distal or opposite direction when tissue is engaged between surfaces 20A and 20B. This preferred shape structure allows for controllable compression of the thick targeted tissue volumes T centrally exposed to the energy delivery means and helps prevent conductance of thermal effects to collateral tissue regions CT (see FIG. 4) and as will be described in greater detail below.

FIGS. 2A and 3 show that first tissue-engaging surface 20A defines an open structure of at least one aperture or passageway indicated at 45 that allows vapor to pass therethrough. The apertures 45 may have any cross-sectional shape and linear or angular route through surface 20A with a sectional dimension C in this embodiment ranging upwards from micron dimensions (e.g., 0.5 μm) to about 2.0 mm in a large surface 20A. The exemplary embodiment of FIG. 3 has an expanding cross-section transition chamber 47 proximate to the aperture grid that transitions between the distal end 34b of chamber 30 and the apertures 45. However, it should be appreciated that such a transition chamber 47 is optional and the terminal portion of chamber 30 may directly exit into a plurality of passageways that each communicate with an aperture 45 in the grid of the first engaging surface 20A. In a preferred embodiment, the second tissue-engaging surface 20B defines (optionally) a grid of apertures indicated at 50 that pass through the loop 22B. These apertures 50 may be any suitable dimension (cf. apertures 45) and are adapted to generally oppose the first tissue-engaging surface 20A when the surfaces 20A and 20B are in the second closed position, as shown in FIG. 2B.

The electrodes 40A and 40B of working end 10 have opposing polarities and are coupled to Rf generator or electrical source 55. FIG. 3 shows current-carrying wire leads 58a and 58b that are coupled to electrodes 40A and 40B and extend to electrical source 55 and controller 60. In a preferred embodiment of the invention, either tissue-engaging surface optionally includes a sensor 62 (or sensor array) that is in contact with the targeted tissue surface (see FIG. 2A). Such a sensor, for example a thermocouple known in the art, can measure temperature at the surface of the captured tissue. The sensor is coupled to controller 60 by a lead (not shown) and can be used to modulate or terminate power delivery as will be described next in the method of the invention.

Figure 4:
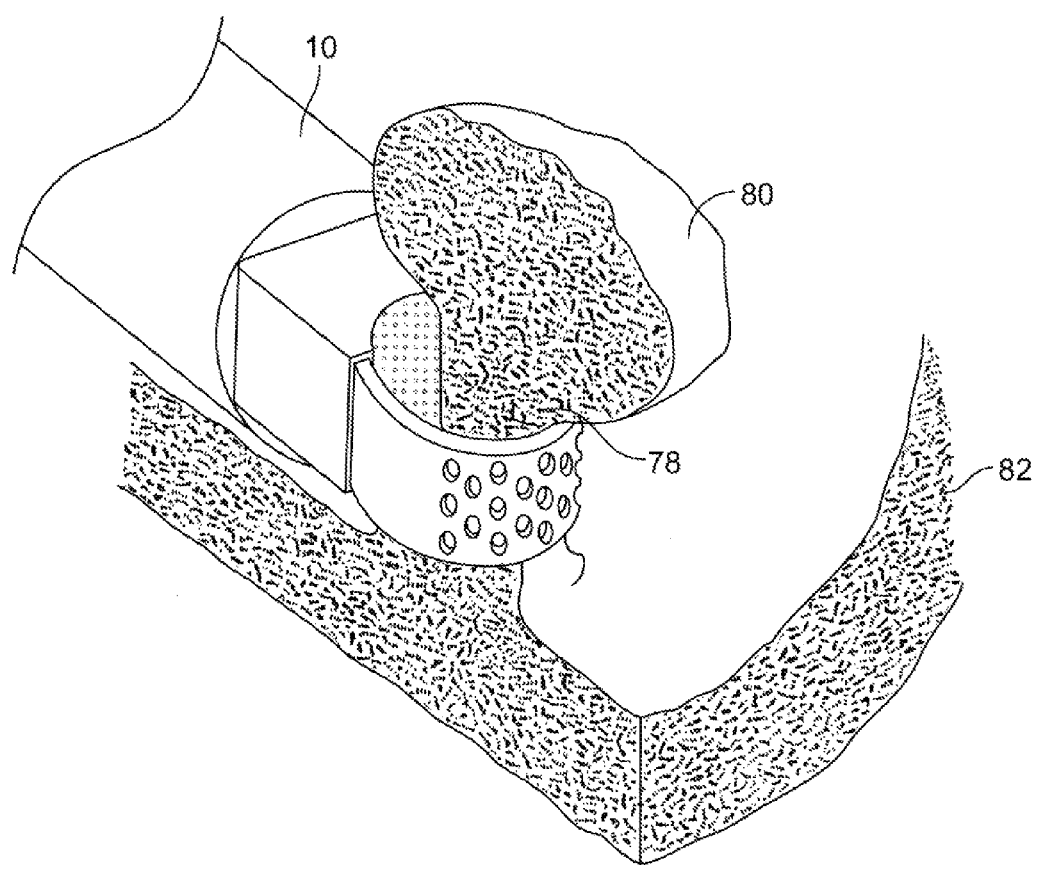
FIG. 4 is a perspective view of the working end of FIG. 3 capturing, an exemplary tissue volume.

Operation and use of the working end of FIGS. 2A, 2B and 3 in performing a method of treating tissue can be briefly described as follows, for example in an endoscopic polyp removal procedure. As can be understood from FIG. 4, the working end 10 is carried by an elongate catheter-type member 12 that is introduced through a working channel 70 of an endoscope 72 to a working space. In this case, the tissue T targeted for sealing is a medial portion 78 of a polyp 80 in a colon 82. It can be easily understood that the slidable movement of the loop member 22B can capture the polyp 80 in the device as shown in FIG. 4 after being lassoed. The objective of the tissue treatment is to seal the medial portion of the polyp with the inventive thermotherapy. Thereafter, utilize a separate cutting instrument is used to cut through the sealed portion, and the excised polyp is retrieved for biopsy purposes.

Figure 5:
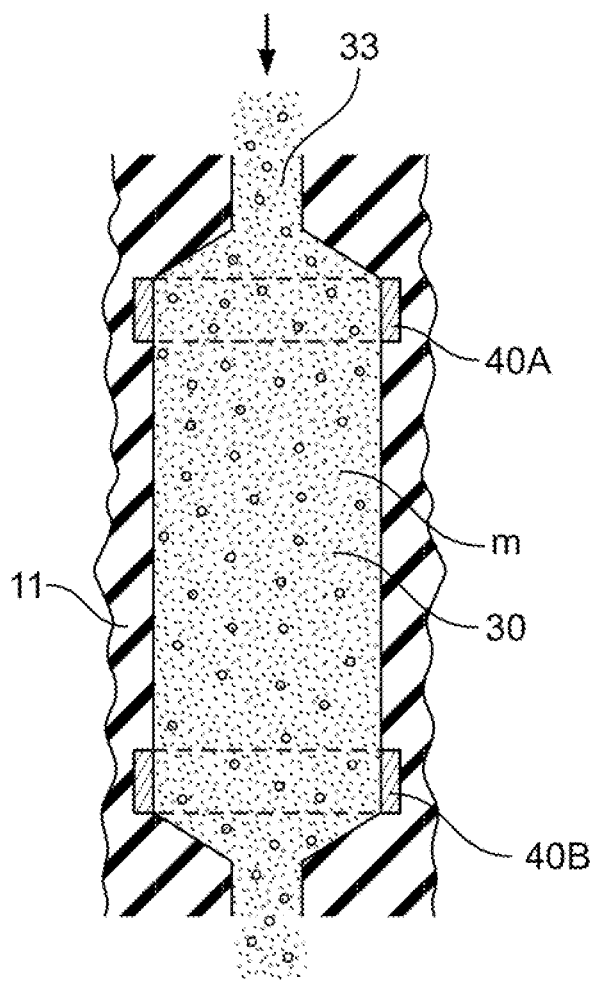
FIGS. 5-6 are sectional schematic views of working end of FIG. 3 depicting, in sequence, the steps of a method of the present invention to seal or weld a targeted tissue volume.
Figure 5:
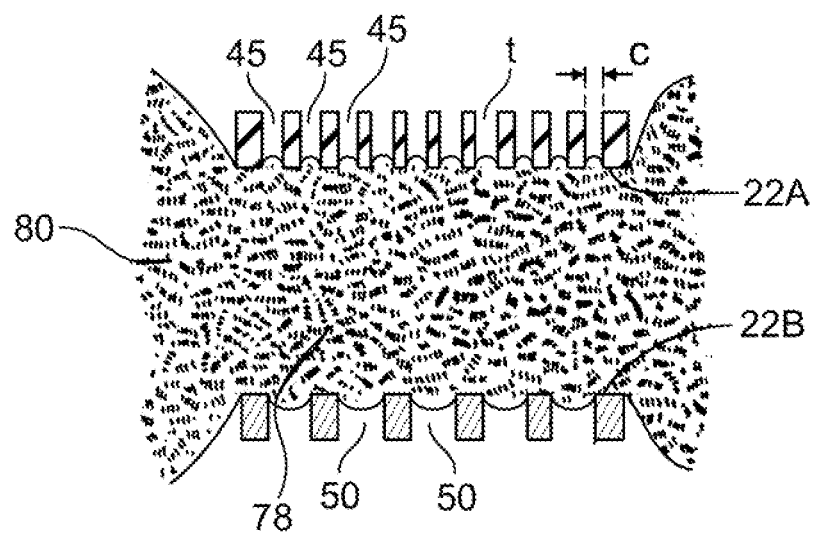
Figure 6:
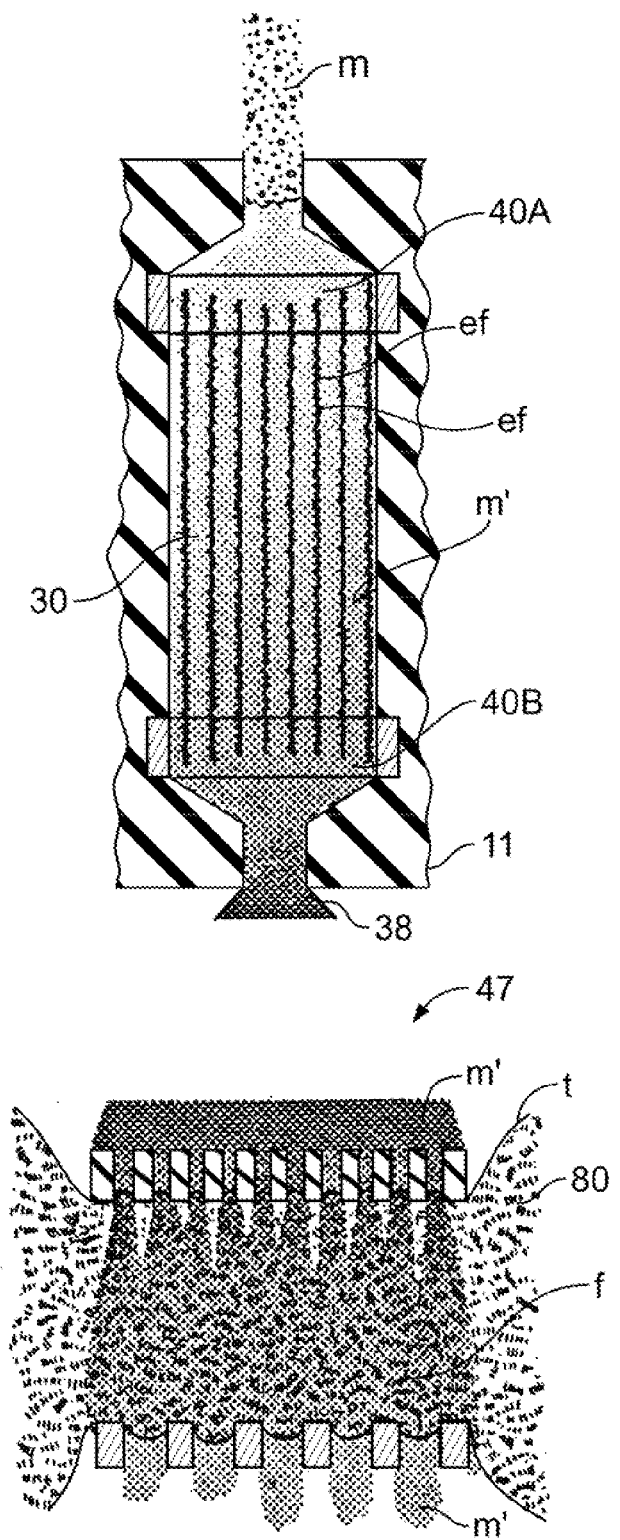

Now turning to FIGS. 5 and 6, two sequential schematic views of the working end engaging tissue T are provided to illustrate the energy-tissue interaction caused by the method of the invention. FIG. 5 depicts an initial step of the method wherein the operator sends a signal to the controller 60 to delivery fluid media M (e.g., saline solution or sterile water) through lumen 33 into chamber 30. FIG. 6 depicts the next step of the method wherein the controller delivers an intense discharge of electrical energy to the paired electrode elements 40A and 40B within chamber 30 indicated by electric arc or electric field EF. The electrical discharge provides energy exceeding the heat of vaporization of the contained fluid volume. The explosive vaporization of fluid media M (of FIG. 5) into a vapor or gas media is indicated at M' in FIG. 6. The greatly increased volume of gas media M' results in the gas being ejected from chamber 30 at high velocity through apertures 45 of surface 20A into the targeted tissue T. The liquid-to-vapor transition caused by the electrical discharge results in the vapor media M' having a temperature of 100° C. or more as well as carrying the heat of vaporization to deliver thermal effects into or through the targeted tissue T, as indicated graphically by the shaded regions of gas flow in FIG. 6. The fluid source and its pressure mechanism can provide any desired level of vapor ejection pressure. Depending on the character of the introduced liquid media, the media is altered from a first lesser temperature to a second greater temperature in the range of 100° C. or higher depending on pressure. The ejection of vapor media M' and its condensation will uniformly and very rapidly elevate the temperature of the engaged tissue to the desired range of about 650 C. to 100° C. to cause hydrothermal denaturation of proteins in the tissue, and to cause optimal fluid inter-mixing of tissue constituents that will result in an effective seal. In effect, the vapor-to-liquid phase transition of the ejected media M' will deposit heat equal to the heat of vaporization (also sometimes called the heat of condensation) in the tissue. At the same time, as the heat of vaporization of media M' is absorbed by water in the targeted tissue, the media converts back to a liquid thus hydrating the targeted tissue T. Such protein denaturation by hydrothermal effects differentiates this method of tissue sealing or fusion from all other forms of energy delivery, such as radiofrequency energy delivery. All other forms of energy delivery vaporize intra- and extracellular fluids and cause tissue desiccation, dehydration or charring which is undesirable for the intermixing of denatured tissue constituents into a proteinaceous amalgam.

The above electrical energy deliver step is continuous or can be repeated at a high repetition rate to cause a pulsed form of thermal energy delivery in the engaged tissue. The fluid media M inflow may be continuous or pulsed to substantially fill chamber 30 before an electrical discharge is caused therein. The repetition rate of electrical discharges may be from about 1 Hz to 1000 Hz. More preferably, the repetition rate is from about 10 Hz to 200 Hz. The selected repetition rate preferably provides an interval between electrical discharges that allows liar thermal relaxation of tissue, that may range from about 10 ms to 500 ms. The electrical source or voltage source 55 may provide a voltage ranging between about 20 volts and 10,000 volts to cause instant vaporization of the volume of fluid media M captured between the electrode elements 40A and 40B. After a selected time interval of such energy application to tissue T, that may range from about 1 second to 30 seconds, and preferably from about 5 to 20 seconds, the engaged tissue will be contain a core region in which the tissue constituents are denatured and intermixed under relatively high compression between surfaces 20A and 20B. Upon disengagement and cooling of the targeted tissue T, the treated tissue will be fused or welded. Over time, the body's wound healing response will reconstitute the treated tissue by means of fibrosis to create a collagenous volume or scar-like tissue.

2. Type "B" Thermotherapy Instrument

Figure 7:
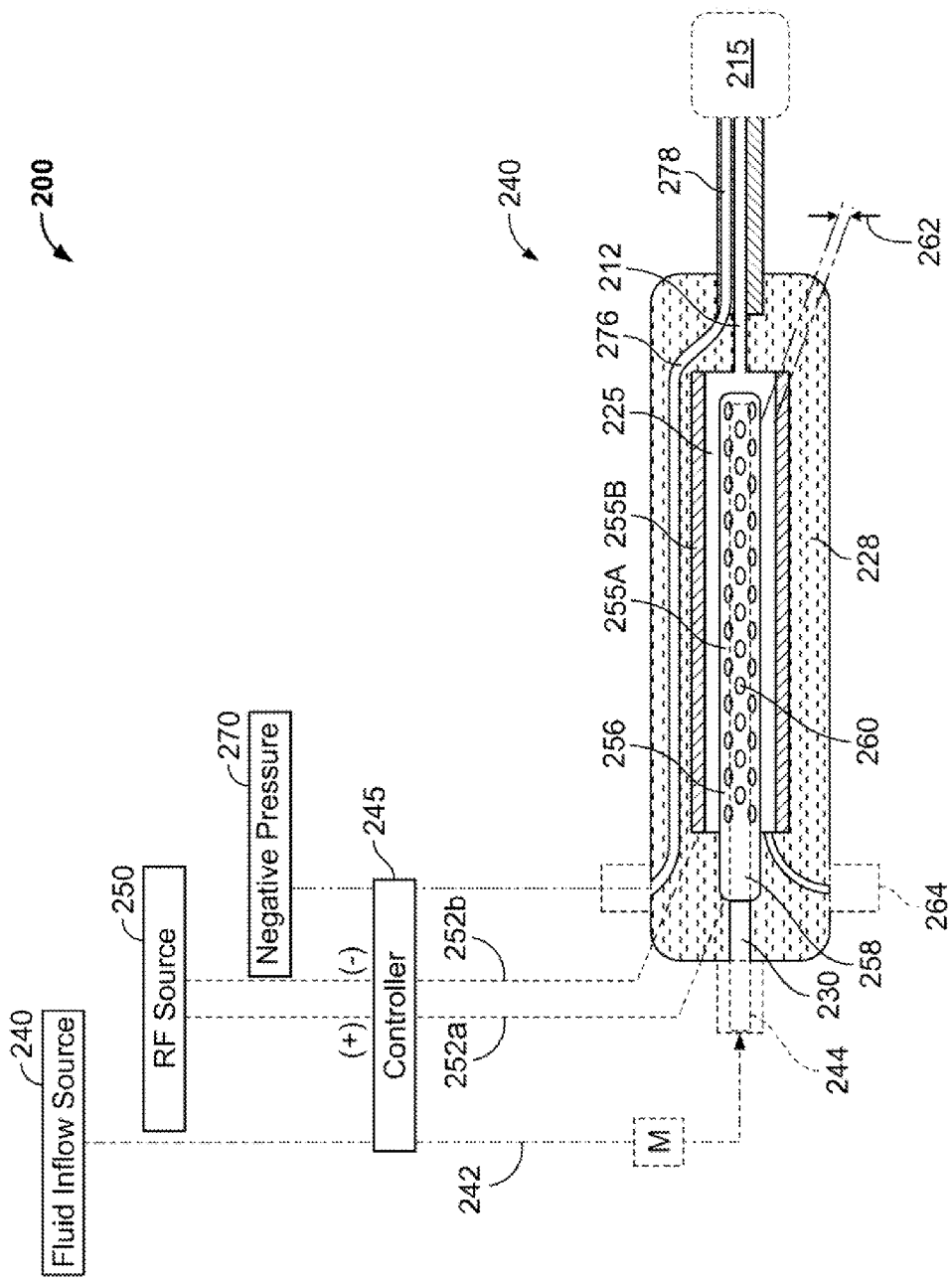
FIG. 7 a cut-away of a Type "B" system with a thermal energy delivery mechanism for a liquid-to-vapor conversion of a pressurized inflow of a saline solution in a probe handle that is coupled to an elongated introducer with a working end configured for delivery of vapor to soft tissue, such as a disc nucleus.
Figure 8:
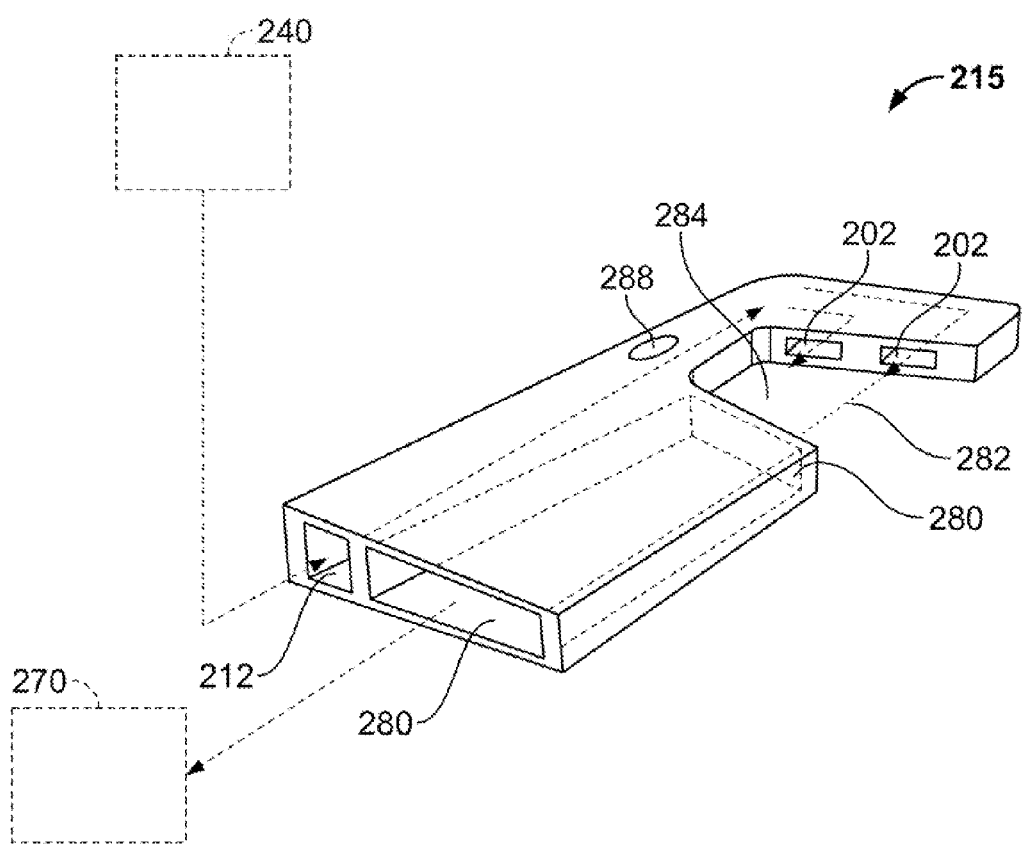
FIG. 8 is view of a working end of the probe of FIG. 7.

Now referring to FIGS. 7 and 8, another embodiment of vapor generation and delivery system 200 is shown. In the previous embodiment, the working end was optimized for engaging and sealing tissue with a working surface that is in contact with tissue. In the embodiment of FIGS. 7 and 8, the working end ejects vapor from port 202 for the controlled application of energy by means of a vapor-to liquid phase change energy release for soft tissue removal, for example, to remove disc nucleus tissue. The system can also be used for removal of other soft tissue such as adipose tissue, tumors and the like. In one embodiment, the vapor quality is adapted for collapse (condensation) as well the high velocity vapor (and vapor droplets) applying mechanical force to the soft tissue to assist in the tissue obliteration. The system and introducer sleeve 205 as shown in FIGS. 7 and 8 also includes a negative pressure source coupled to an outflow lumen or channel for extracting condensed vapor and tissue debris from the targeted site, as will be described in more detail below.

In FIG. 7, it can be seen that system 200 includes a handle portion 204 that transitions into an introducer sleeve 205 that has an elongated dimension for introduction into a patient's body percutaneously, or through a body cavity or a body lumen. The diameter of introducer sleeve 205 can range from about 1 mm to 6 mm or more. In one embodiment, the introducer sleeve is configured for introduction percutaneously into patient's disc as indicated in FIG. 9.

In one embodiment, the introducer sleeve 205 is fabricated of a temperature resistant polymer or a metal in combination with a polymeric coating. The introducer sleeve 205 can be rigid, deformable or articulatable as in known in the art. In one embodiment, the introducer sleeve 205 is a metal coated with a polymer having a low thermal conductivity, for example less than about 1.0 W/m-K, and preferably less than about 0.50 W/m-K. In one example, an unreinforced polyetheretherketone (PEEK) has a thermal conductivity of about 0.25 W/m-K and can be used for inner and/or outer layers of the introducer. Alternatively, the introducer sleeve 205 can be of PEEK. PEEK is high temperature resistant engineered thermoplastic with excellent chemical and fatigue resistance plus thermal stability. PEEK had a maximum continuous working temperature of 480° F. and retains its mechanical properties up to 570° F. in high-pressure environments. Other materials used in the introducer can comprise formulations or blends of polymers that include, but are not limited to PTFE, polyethylene terephthalate (PET), or PEBAX, PTFE (polytetrafluoroethylene) is a fluoropolymer which has high thermal stability (up to 260° C.), is chemically inert, has a very low dielectric constant, a very low surface friction and is inherently flame retardant. A range of homo and co-fluoropolymers are commercialized under such names as Teflon®, Tefzel®, Neoflon®, Polyvflon® and Hyflon®. In another embodiment, the introducer sleeve can carry another layer of a suitable thickness that comprises a low thermal conductivity region such as an air gaps, a layer of an insulative ceramic or glass microspheres or fibers, or at least one lumen that carries a cryofluid in communication with a cryogenic fluid source as in known in the art.

Now turning to FIG. 7, the cut-away view of handle 204 shows that an interior chamber 225 is formed within the interior of an insulator material indicated at 228 such as a ceramic or a combination of materials to insulate the interior chamber 225 from the surface of the handle. An inflow channel 230 communicates with pressurized inflow source 240 of fluid or liquid media via flexible tube 242 coupled to fitting 244. A computer controller 245 is provided to control parameters of fluid inflows to the interior chamber 225. The interior chamber 225 has a distal region in which media flows transition to outflow channel 212 that extends to the working end 215. In FIG. 8, it can be seen that Rf source 250 (also operatively connected to controller 245) has first polarity (+) lead 252a and opposing second polarity (−) lead 252b that are coupled respectively to first and second conductive surfaces or electrodes 255A and 255B exposed in interior chamber 225 that serve as a thermal energy delivery mechanism. The first conductive surface 255A is the outer surface of elongated sleeve 256 with bore 258 therein having diffuser ports 260 in the sleeve wall for introducing pressurized liquid media M into the interior chamber 225. The diffuser ports 260 have a suitable dimension and configuration for diffusing or atomizing a high pressure inflow of flow media M from source 240, which preferably is a saline solution. The second polarity (−) lead is coupled to conductive surface 255B which comprises a radially outward surface of interior chamber 225. In the embodiment shown in FIG. 7, it can be seen that the first and second conductive surfaces 255A and 255B are concentric, extend over a substantial length of the handle and have a large surface area with a fixed spaced apart radial dimension indicated at 262. The radial dimension 262 between the electrode surfaces is selected to match the particular impedance and other operating characteristics of the Rf generator.

The system also includes a negative pressure source 270 that communicates with an outflow channel 276 and outflow lumen 278 in the introducer sleeve, as can be seen in the cut-away view of FIG. 7. In FIG. 8, it can be seen that the working end 215 has a suction port 280 that is configured for the aspiration of tissue debris from the targeted site. The ablation, obliteration and volumetric removal of soft tissue is enabled by the phase change energy release of the vapor transitioning to a liquid as well as mechanical effect of vapor engaging the soft tissue. In the embodiment of FIG. 8, the vapor outlet (or a plurality of outlets) 202 (i) eject vapor along an axis 282 in a recess 284 that is at least in partly oriented toward an axis of the aspiration port 280, or (ii) that deflect vapor toward at least one aspiration port 280. In any embodiment, the inflow pressure of the media can range upward from about 5 psi. In this embodiment, the inflow pressure is elevate greatly to the range of about 5,000 psi to 50,000 psi with a very small media outlet in the range of 0.005" to 0.025" or other suitable dimension and pressure wherein water droplets can apply mechanical energy to scour, damage or obliterate soft tissue. In this embodiment, the system includes the Rf source 250 described above that are operatively coupled to the media inflow pressure source 240 and controller 245 that can apply energy to cause a selected level of vaporization. Optionally, the system can be configured to pulse the energy delivery or the vapor flows at 10 Hz to 500 Hz which it has been found is useful for soft tissue removal. In one method of use, the system can control pressure and flow volume for allowing the vapor flow to obliterate or scour soft disc nucleus tissue while not allowing obliteration of the disc annulus. The system thus allows for tissue discrimination and ablation based on tissue characteristics such as tissue density, tissue fibrous level and the like. The working end 215 of FIG. 8 is thus well suited for volumetric removal of disc nucleus tissue. Such treatments are needed for new procedures that implant an artificial nucleus, for annulus repair treatments.

Referring to FIG. 7, in a method of operation, the system injects a volume of liquid saline flow media M at a selected rate under pressure from source 240 which is diffused and atomized by ports 260 as the media enters interior chamber 225. Contemporaneous with injection and diffusion of the volume of saline, the system delivers sufficient current from source 250 and controller 245 to the conductive atomized saline via the opposing polarity surfaces 255A and 250B which instantly vaporize the $H_2O$ in the flow media M to generate a vapor M' that is injected from interior chamber 225 into lumen or channel 212 of introducer sleeve 205. The instantaneous increase in volume of media in the liquid-to-vapor phase transition greatly increases interior pressures in interior chamber 225 to thereby accelerate the flow into and through the introducer sleeve to working end 215. Contemporaneous with the ejection of vapor from the working end, the negative pressure source 270 is actuated to suction the collapsing vapor and tissue debris into port 280 and aspiration channel 278. In any embodiment, the vapor aspiration port or ports 280 are substantially larger in cross-section than the vapor outlet or outlets 202 to accommodate the increase in volume of the condensate as well as tissue debris.

Turning back to FIG. 7, the system and handle 204 can include an optional pressure relief valve schematically indicated at 264 so that any overpressures in the interior chamber are released. The release of any overpressure can be vented through an additional lumen in the supply tube 242 or to another chamber in the handle.

Figure 9A:
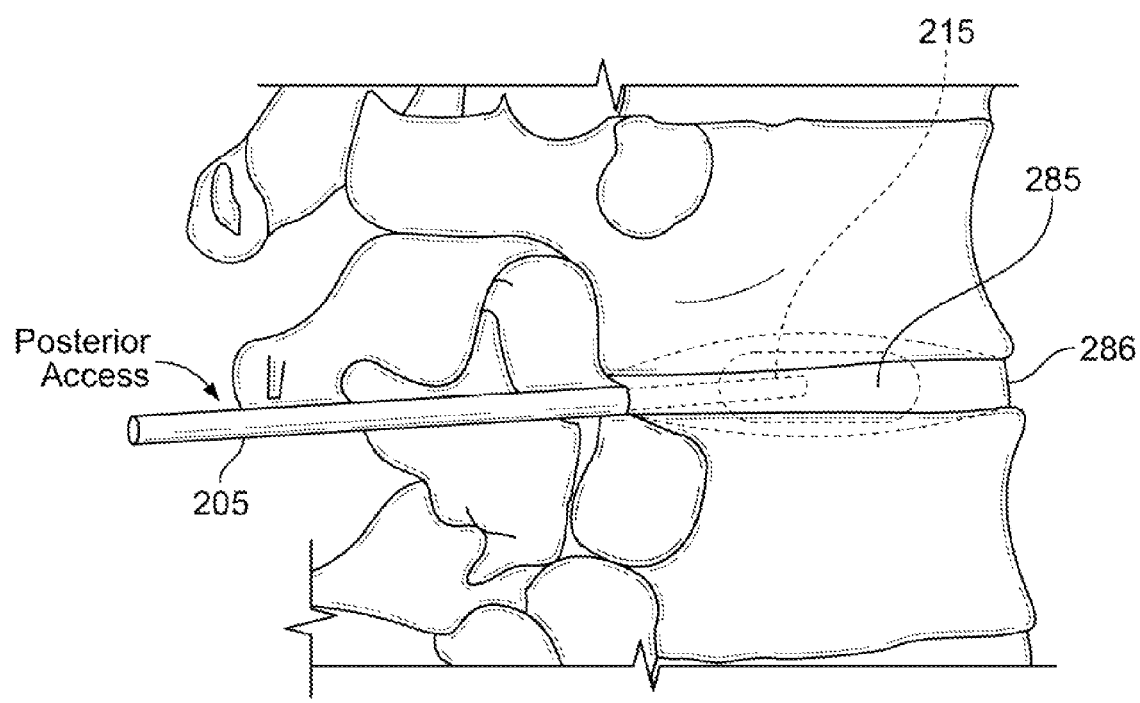
FIG. 9A is a view of a method of using the probe working end of FIG. 8 to volumetrically remove disc nucleus tissue.

FIG. 9A further depicts a method of the invention in treating a patient's disc for removal of a disc nucleus. In FIG. 9A, it can be seen that the physician has navigated the working end 215 to the targeted nucleus region 285 of a disc 286 as in known in the art under imaging, such as fluoroscopy. In one embodiment, the working end carries radiopaque marking to allow the physician to see the angular orientation of the working end. In a next step, the physician sets the pressure, volume of vapor and rate of vapor delivery in the fluid inflow controller 245 that is operatively coupled to the fluid source 240, Rf source 250 and negative pressure source 270. The controller 245 operates from pre-sets that select a power level and duration of Rf energy delivery to cooperate with the selected volume of inflowing media M. The controller 245 also operates using pre-sets for simultaneous actuation of the negative pressure source 270 that communicates with lumen 278 in introducer sleeve 205 for suction of tissue debris and vapor condensate. The physician then can move the working end 215 axially, rotationally and angularly to remove the disc nucleus while the preventing damage to the annulus.

Figure 9B:
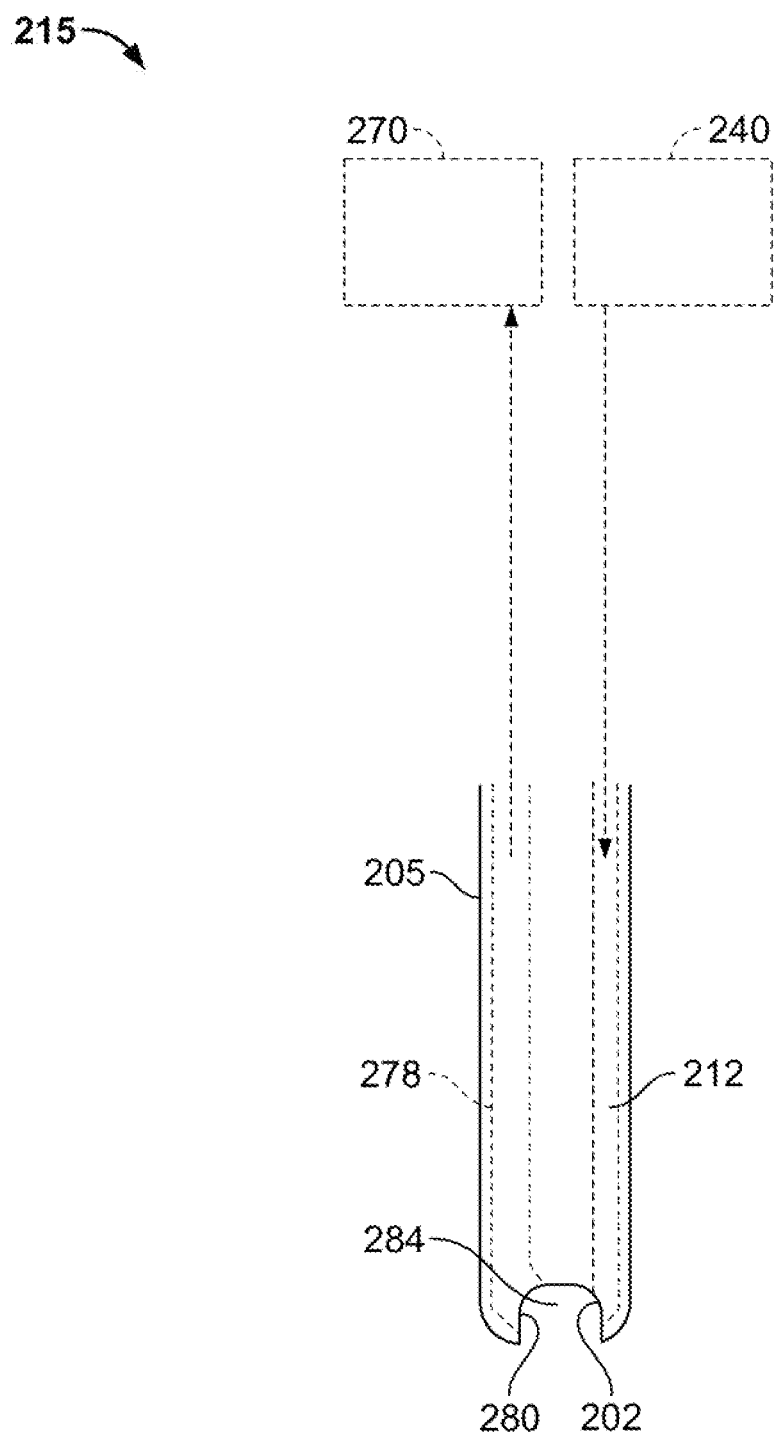
FIG. 9B is a view of an alternative working end similar to FIG. 8.
Figure 9C:
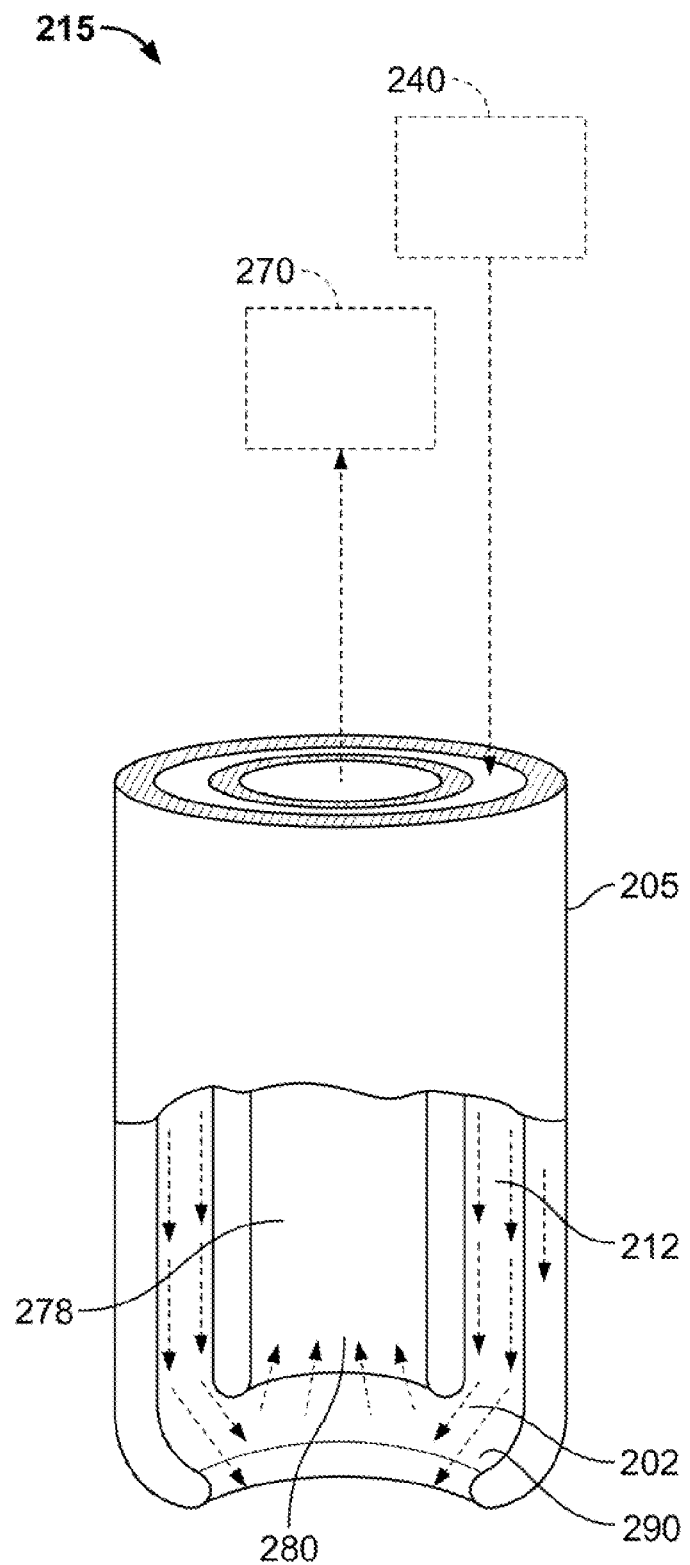
FIG. 9C is a view of another alternative working end similar to FIGS. 8 and 9B.
Figure 9D:
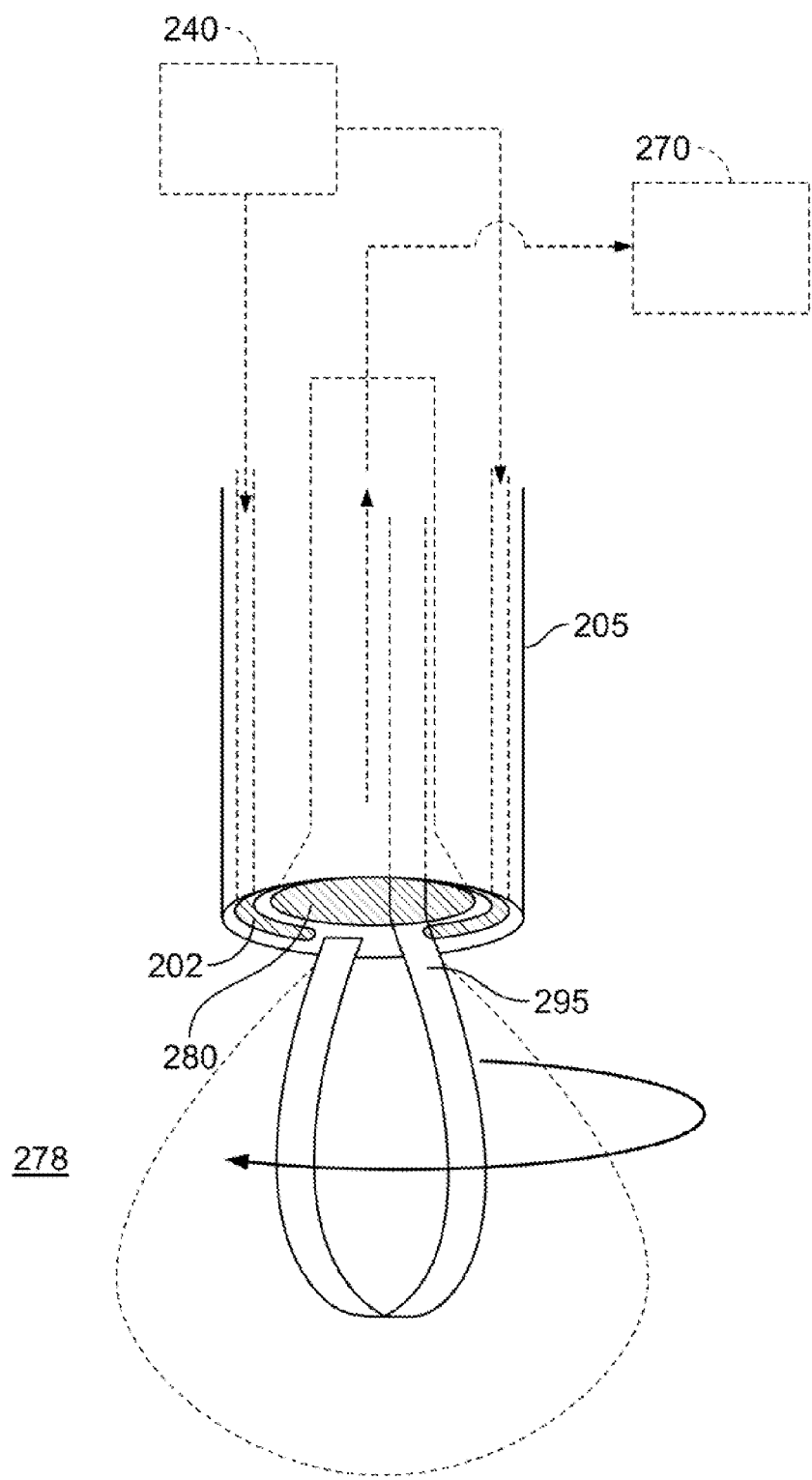
FIG. 9D is a view of another alternative working end similar to that of FIG. 9C with a cutting loop for cutting soft tissue.

FIGS. 9B and 9C illustrate working ends 215 that are similar to that of FIG. 8 with different arrangements of vapor outlets 220 and aspiration ports 280. In FIG. 9B, a recess 284 is at the distal end the introducer sleeve 205 with the vapor outlet 220 and aspiration port 280 generally opposing on another in the recess. In FIG. 9C, the introducer 205 includes a deflector portion indicated at 290 proximate the vapor outlet 202 for deflecting the flow of vapor toward the aspiration port. In the embodiment of FIG. 9C, the vapor inflow channel 212 and the aspiration channel 278 are in a concentric configuration. FIG. 9D illustrates a working end wherein the introducer sleeve 205 is rotatable at high speed together with a loop element 295 that can be deployed from the working end to cut or scour tissue contemporaneous with energy delivery as described above. The loop element can rotate at any speed from about 20 rpm to 10,000 rpm. In one embodiment, the loop 295 is made of a flexible, round cross-section polymer filament. In use, the filament will operate to cut soft tissue but flex to discriminate against cutting harder tissue. This system is useful in discriminating, for example, between the disc nucleus and the annulus. In another embodiment, the loop 295 is a metal with option blade edge that can be used, for example, to excise and extract soft tumor tissue in a breast, liver, lung or the like. The energy delivered by the vapor contemporaneously obliterates the tissue and can thermally seal the cavity created by the tissue extraction.

An optional pressure sensor 288 located at the distal end of the introducer 205 (FIG. 8) can be used to assist in determining pressures in the interior of the patient in a working region. MEMS-fabricated pressure sensors are known in the art and can be carried in the surface of the introducer or the balloon surface, for example, of the type fabricated by Integrated Sensing Systems, Inc., 391 Airport Industrial Drive, Ypsilanti, Mich. 48198. Such sensor can be linked back to controller 245 to adjust aspiration pressures or to terminate vapor flow. The MEMS sensor also can be an accelerometer linked to the controller for modulating or terminating vapor delivery in response to unwanted movement of the working end caused by the high pressure ejection of vapor.

Figure 10:
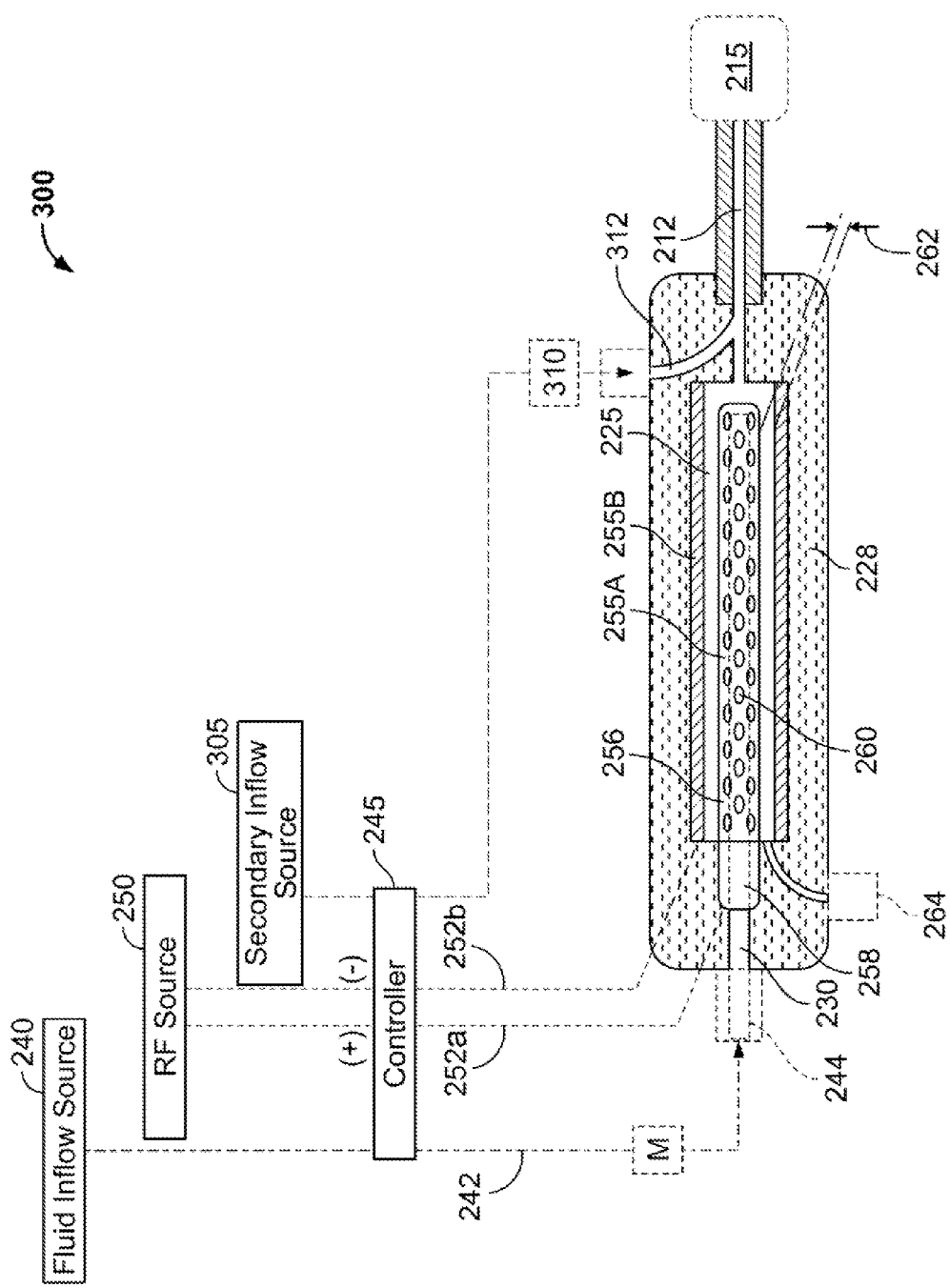
FIG. 10 is another embodiment similar to that of FIG. 7 with an alternative system for delivering vapor to soft tissue together with introducing a second media to control the mass average temperature of the vapor.

In another embodiment and method of the invention, referring to FIG. 10, the system 300 can include a secondary pressurized media inflow source 305 that is adapted to introduce media or substance 310 (in the form of at least one of a gas, liquid or particulate) through channel 312 in the handle into channel 212 to combine with vapor media M' after it is ejected from chamber 225. In a method of the invention, the system thus allows for controlling the average mass temperature of the vapor. In one embodiment, the additional media 310 comprises a bioinert gas or atomized fluid that is depressurized and introduced into the vapor for the purpose of reducing the mass average temperature of the injected media to lower than about 100° C. For example, the introduced media 310 can be depressurized CO2, N2, or O2 or atomized H20. By this means, the mass average temperature can be less than 100° C., for example in the range of about 45° C. to 100° C. More preferably, the mass average temperature can be in the range of about 60' C. to 95° C. Still more preferably, the mass average temperature can be in the range of about 70° C. to 90° C.

Figure 11:
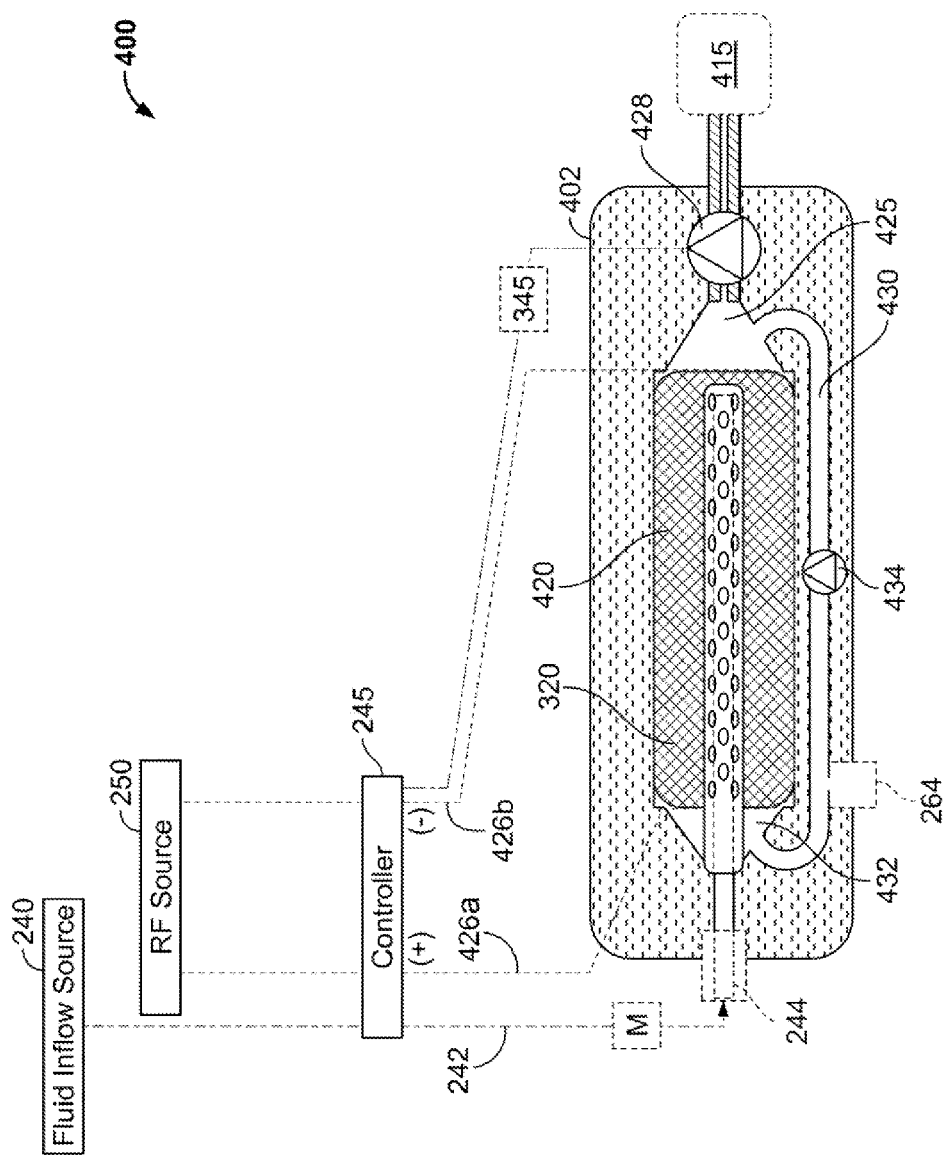
FIG. 11 is another embodiment similar to that of FIG. 11 with an alternative system for delivering thermal energy.

FIG. 11 illustrates another system embodiment 400 with handle 402 that utilizes a resistive element 420 in interior chamber 425 to cause the liquid-to-vapor phase change in the inflowing media M. All other system components are similar to the previous embodiments and have similar reference numbers. The electrical leads 426a and 426b in this embodiment are coupled to opposing ends of resistive element 420. In one embodiment, the resistive element 420 comprises a flow permeable structure such as a syntactic material or open-cell material (FIG. 11). The terms "syntactic", "open-cell" and "flow permeable" as used herein refer to any structure that has substantial porosity for allowing fluid flow therethrough. Such materials have the advantage of providing very high surface areas for conducting heat from an I2R heated material to pressurized media flows therein. The syntactic structure is further selected to provide an internal pore dimension that causes diffusion and atomization of high pressure inflows, for example of sterile water or saline. For example, the resistive element 420 can comprise a syntactic metal, resistive ceramic composite, or include a carbon portion. Such materials are available from ERG Materials and Aerospace Corp., 900 Stanford Avenue, Oakland, Calif. 94608 and Poco Graphite (http://www.poco.com). The open-cell material also can be an open cell foam that is metal plated, a sintered material, a plated entangled filament material, or any ordered or disordered structure commonly known in the art.

In the embodiment of FIG. 11, the system further includes a valve system 428 and recirculating channel 430 that are adapted for controlling the generation and release of vapor from working end 415. In the previous embodiments, the use of Rf energy delivery for vapor generation in chamber 225 (FIG. 7) can cause instantaneous high pressure flows of vapor. In the system embodiment of FIG. 11, the delivery of energy by means of resistive element 420 can require a fraction of a second or more to produce vapor from high pressure inflows of liquid media M. For this reason, the interior chamber 425 includes a recirculation channel 430 for a looped flow of vapor—or vapor and water droplets—that circulates back to inflow channel or the proximal end 432 of interior chamber 425. It should be appreciated that the recirculation channel 430 can be entirely housed in handle 402 or can circulate back to the source 245 or another intermediate chamber. The recirculation channel 430 also is operatively coupled to a pressure relief valve 262 as described above, and can further include a one-way valve indicated at 434. In operation of the embodiment, the system is actuated to create vapor which can circulate until a switch 435 coupled to controller 245 and valve 428 is actuated to release vapor M' from interior chamber 425. In all other respects, the method of the invention is the same as described above.

The schematic view of system 400 in FIG. 11 depicts the valve 428 in the handle, but the valve can also be located in working end 415 or elsewhere in introducer sleeve 205. Such valve systems can be linked to controller 245 by electrical leads in the introducer wall. In another embodiment, the valve 428 can be in the working end 415 and the recirculation channel 430 also can extend through the introducer sleeve 205 to the working end 415. This system thus assures that high quality vapor will be ejected from the working end.

The scope of the invention includes the use valve system 428 and recirculating channel 430 in other embodiments that utilize Rf, laser microwave or other energy deliver mechanisms. For example, in an Rf energy system as in FIG. 7, the valve and recirculating channel 430 systems can be used to control slight inconsistencies in vapor generation due to varied liquid inflow rates that sometimes results in sputtering and incomplete vaporization or inflowing media.

In another embodiment similar to that of FIG. 11, the system can infuse heated water (or saline or another liquid) from an external source wider high pressure into an enclosed interior chamber of the system. The system also includes a valve similar to valve 428 in FIG. 11. Upon opening of the valve, the release of pressurized fluid will in part release the energy that was exerted on the fluid in the form of pressure—which will be converted into the energy required to vaporize the heated fluid. This type of system has the advantage of not requiring a thermal energy source with sufficient capacity for vaporizing needed volumes of vapor. Instead, a pressurization mechanism combined with a less robust thermal energy delivery system can be used to produce the required volume of vapor. Such sources can be external to the handle of the introducer.

The scope of the invention included use of the system to apply energy from a phase-change release to tissue for tissue modification in various procedures. The system can be configured with a needle-like working end to treat tumor tissue in a prostate, liver, kidney, breast, lung, vertebra and the like. The system can be configured with a needle-like working end for ablating fibroids. In another embodiment, a very small gauge needle (e.g., 36 ga.) can be used with fiber optic viewing to treat macular degeneration for shrinking and sealing leaking microvasculature. As very small gauge needle also can be used in a vision correction treatment to treat the cornea. A series of spots around the cornea can be targeted with vapor to shrink collagen to create a steepened cornea for treating presbyopia or to treat hyperopia. In another embodiment, the system can use a phase change energy release in an endometrial ablation procedure. In another embodiment, the system can use a small gauge blunt-tipped vapor delivery device that used pulses of vapor to cut brain tissue without causing any collateral thermal damage. A similar device can be used in orthopedic surgery to cut ligaments, cartilage and the like. The system can use in a cutting loop for TURP procedures. The system also can be used for delivering energy to a body lumen such as a blood vessel. In another embodiment, the system can be used to shrink lung tissue to cause lung volume reduction.

3. Type "C" Embodiment of Working End for Energy Delivery.

Figure 12:
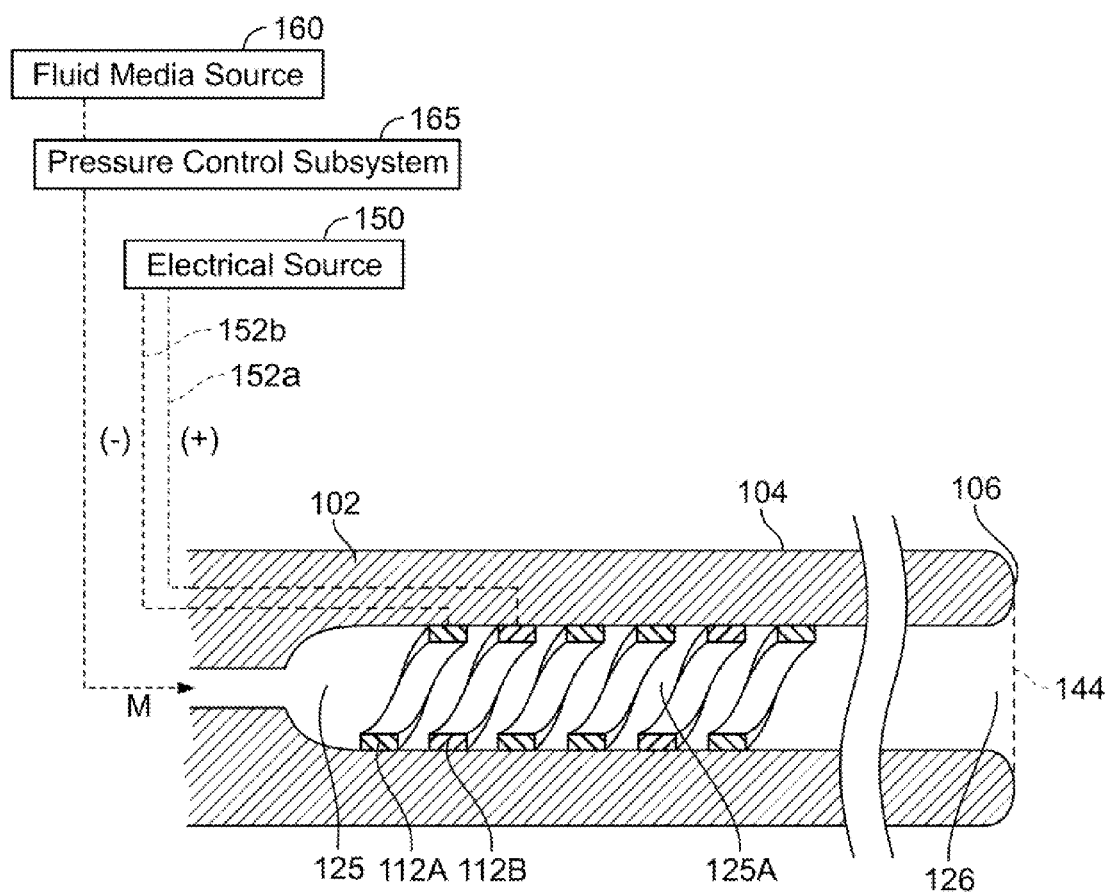
FIG. 12 is a sectional view of a Type "C" embodiment of an instrument working end for applying energy to tissue, and is more particularly for thermal treatment of endoluminal body structure.

Now referring to FIG. 12, an alternative Type "C" embodiment of instrument working end 100 is shown in sectional view. In this Type "C" embodiment, the system utilizes an apparatus and the thermal effects are controlled—but the application of energy is designed to cause a selected level of thermal effects in endovascular tissue, or in body media within or about other body lumens, ducts and the like.

FIG. 12 illustrates the working end 100 of a member or catheter body 102 that is dimensioned for introduction into a patient's vasculature or other body lumen. The diameter of body 102 can range from about 1 Fr. to 20 Fr. The working end 100 typically is carried at the distal end of a flexible catheter but may also be carried at the distal end of a more rigid introducer member. In a rigid member 102, the working end also can be sharp for penetrating into tissue or into the lumen of a vessel.

The working end 100 of FIG. 12 defines a surface 104 which extends about the radial outward surface of the member and the distal terminus 106. The working end again carries opposing polarity electrodes 112A and 112B as thermal energy emitters in an interior bore or lumen 125 that terminates in a media entrance port 126 in the distal terminus 106. The bore may have a very small diameter (e.g., ranging in diameter from about 5 microns to 25 microns or equivalent cross-section), or alternatively a cross-section ranging between 0.2 mm. and 2.0 mm. in diameter or equivalent cross-section. In this embodiment, the electrodes 112A and 112B are spaced apart, indicated with (+) and (−) polarities, and configured in an intertwined helical configuration to provide a substantially large surface area for exposure to fluid media M. The electrodes can extend axially from about 1 mm. to 50 mm. This type of electrode arrangement will enhance energy delivery to the fluid to allow effective continuous vaporization thereof. As shown in FIG. 12, the electrodes can be recessed into bore 125 from the distal end by any dimension ranging from about 10 microns to 100 mm. or more. The working end again defines a lumen portion 125A between the electrodes 112A and 112B wherein energy application is focused to create the desired energy density in the in flowing fluid media M, in this case to cause its immediate vaporization. The type of energy delivery provided by the working end 100 relates to controlled thermal effects. The superheated vapor is propagated across the interface 144 defined by the working, surface 104 that carries the open port 126, which in this embodiment comprises the distal most surface of member 102. It should be appreciated that the instrument may have a plurality of media entrance ports 126 in surface 104 of the member 102, for example to apply energy radially outward as well as distally.

In the system embodiment of FIG. 12, the electrodes 112A and 112B are coupled to electrical source 150 by leads 152*a* and 152*b*. The working end 100 also is coupled to fluid media source 160 that carries pressurization means of any suitable type together with a pressure control subsystem indicated at 165. Such systems operate as described in U.S. Pat. No. 6,911,028.

Figure 13:
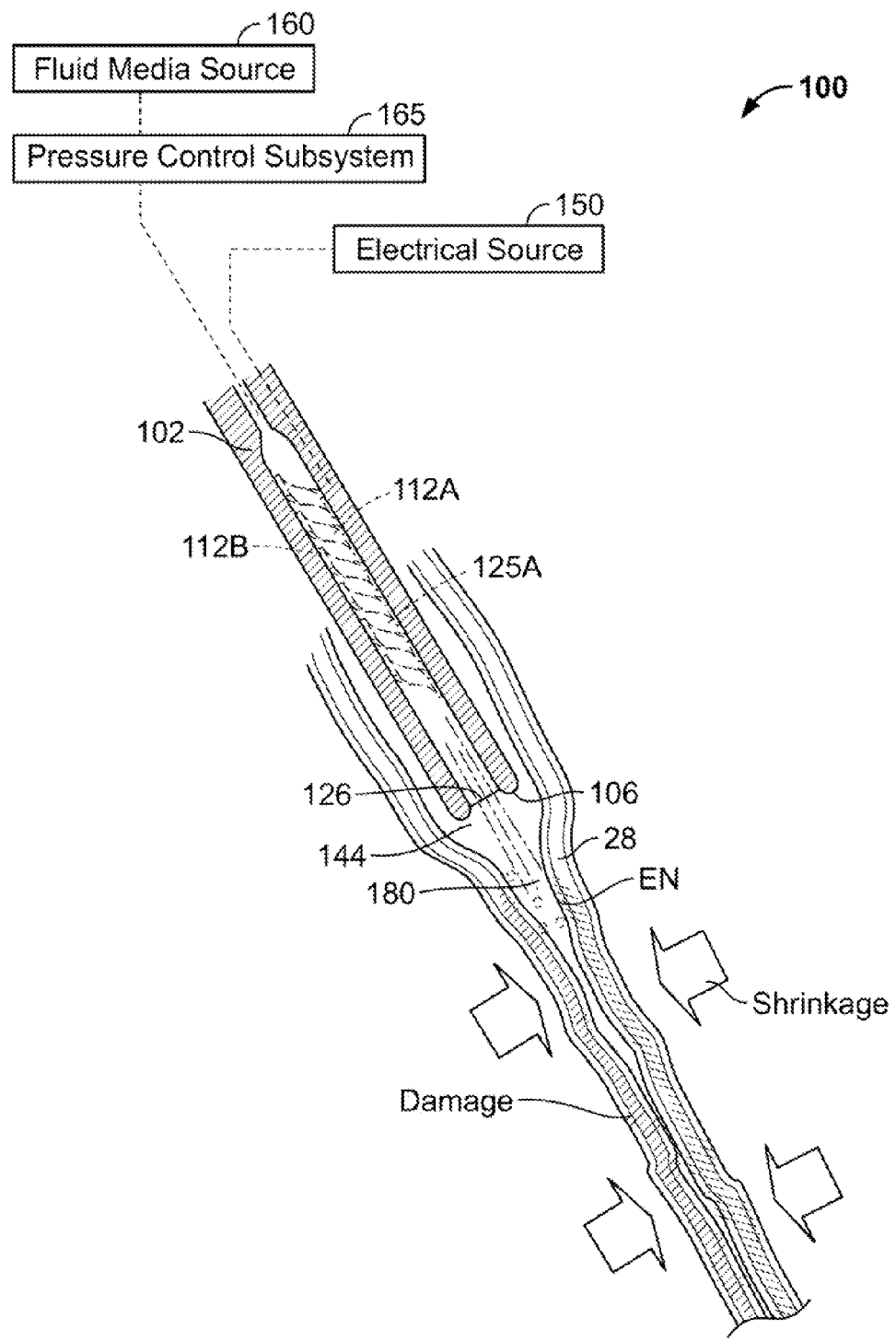
FIG. 13 is a sectional view of the instrument working end of FIG. 12 depicting a method of the invention in applying energy to tissue to cause thermal effects in an endoluminal environment.

In FIG. 13, the method of the invention is shown graphically wherein the distal end 100 is introduced into vasculature for the purpose of creating thermal effects in the vessel walls 28, its endothelial layer EN or blood. In one targeted endovascular procedure, as depicted in FIG. 13, the objective is to apply controlled thermal energy to tissue to shrink and/or damage vessel walls to treat varicose veins. Most endothelial-lined structures of the body, such as blood vessel and other ducts, have substantially collagen cores for specific functional purposes. Intermolecular cross-links provide collagen connective tissue with unique physical properties such as high tensile strength and substantial elasticity. A well-recognized property of collagen relates to the shrinkage of collagen fibers when elevated in temperature to the range 60° to 80° C. Temperature elevation ruptures the collagen ultrastructural stabilizing cross-links, and results in immediate contraction in the fibers to about one-third of their original longitudinal dimension. At the same time, the caliber of the individual collagen fibers increases without changing the structural integrity of the connective tissue.

As represented in FIG. 13, the delivery of energy from the electrodes 112A and 112B to an inflow of fluid media, such as any saline solution, will cause its instant vaporization and the expansion of the vapor will cause high pressure gradients to propagate the heated vapor from the port 126 across interface 144 to interact with endovascular media. The pressurized fluid media source 160 and pressure control subsystem 65 also can be adapted to create a pressure gradient, or enhance the pressure gradients caused by vapor expansion, to controllably eject the heated vapor from the working surface 104. As seen in FIG. 13, the vaporized media 180 can transfer heat, effectively by means of convective heat transfer, to the vessel walls. The vaporized media is at about 100° C. as it crosses the interface 144 and pushes blood distally while at the same time causing the desired thermal effects in the vessel wall.

As shown in FIG. 13, the collagen in the vessel walls will shrink and/or denature (along, with other proteins) to thereby collapse the vessel. This means of applying thermal energy to vessel walls can controllably shrink, collapse and occlude the vessel lumen to terminate blood flow therethrough, and offers substantial advantages over alternative procedures. Vein stripping is a much more invasive treatment. Rf closure of varicose veins as known in the art uses Rf electrodes to contact the vessel walls to collapse and damage the walls means of causing ohmic heating in the vessel walls. Such Rf ohmic heating cause several undesirable effects, such as (i) creating high peak electrode temperatures (up to several hundred degrees C.) that can ohmic heating and damage in nerves extending along the vessel exterior, (ii) causing non-uniform thermal effects about valves making vessel closure incomplete, and (iii) causing vessel perforations in introducing the catheter-type instrument that is dragged along the vessel walls. In contrast, the energy delivery system of the invention utilizes heated vapor that cannot exceed 100° C. to apply energy to the vessel walls which is substantially prevents heat from being propagated heat outwardly by conduction—thus preventing damage to nerves. There is no possibility of causing ohmic heating in nerves, since a principal advantage of the invention is the application of therapeutic heat entirely without electrical current flow in tissue. Further, the vapor and its heat content can apply substantially uniform thermal effects about valves since the heat transfer mechanism is through a heated gas that contacts all vessel wall surfaces—and is not an electrode that is dragged along the vessel wall. Further, the vapor 180 can be propagated from the working end 100 while maintained in a single location, or a plurality of locations. Thus, the system of the invention may not require the navigation of the member 102 through tortuous vessels. Alternatively, the working end 100 may be translated along the lumen as energy is applied by means of convention.

Another advantage of the invention is that the system propagates a therapeutic vapor media from the working end surface 104 that can be imaged using conventional ultrasound imaging systems. This will provide an advantage over other heat transfer mechanisms, such as ohmic heating, that cannot be directly imaged with ultrasound.

The working end 100 and its method of use as depicted in FIGS. 12-13 can to apply therapeutic heat to blood vessel wall to treat chronic vascular insufficiency (CVI). In this disorder, venous valves are impaired or non-functional due in part to vessel swelling and distention proximate to the valves. The working end 100 as depicted in FIG. 13 can be positioned within the vessel to apply heat to the distended vessel wall portions to restore venous valve function, intraoperative ultrasound can be used to image the procedure. The working end 100 and method can also be used to shrink AVMs (arterial vascular malformations) and aneurysms.

In another method of the invention, the working end 100 as depicted in FIGS. 12-13 can be used to apply therapeutic heat to any duct, cavity, lumen, septae or the like in the body to shrink, collapse or damage the anatomic walls or to fuse together and seal endothelial layers thereof. For example, the system and method can be used for tubal ligation in a treatment of fallopian tubes, or for closing microvasculature terminate blood flow to vascularized diseased tissue, tumors and the like. Such embolic, vessel closure methods are used to starve cancerous tissues and fibroids from blood flow. Such vessel closure methods are also can be used to starve blood flow from alveoli in a lung volume reduction procedure for treating emphysema. The working end 100 can also be introduced within the patient's airways to directly deliver therapeutic heat to airways to cause their collapse to cause lung volume reduction.

The above Type "C" system and methods have been described for use in endoluminal environments wherein the propagation of heated matter (vapor) can function optimally (i) within a fluid in the lumen, (ii) by displacing the fluid in the lumen, or (iii) by expanding, a space within a collapsed lumen, duct, septae or the like. It should be appreciated that the systems and methods of the invention also can be used to apply energy directly to the interior of soft tissue volumes, for example to kill tumors. The heat vapor will propagate within extracellular spaces to thereby cause therapeutic heating for any purpose.

The Type "C" system described above has opposing polarity electrodes to deliver energy to the inflowing fluid media. In an alternative embodiment (not shown), a resistive element can be used made out of any suitable material such as tungsten. The system can apply high levels of energy to the resistive element that interfaces with the inflowing fluid media. The superheated resistive element can vaporize the fluid media as describe above. The resistive element can be helical, tubular or a microporous structure that allows fluid flow therethrough.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

We claim:

1. A method of treating a tissue of a patient, the method comprising:
   generating a vapor that carries a therapeutic heat, where generating the vapor comprises delivering a fluid media within a device chamber and applying energy the fluid media in the device chamber to cause vaporization of the fluid media to the vapor, recirculating any fluid media that incompletely vaporized back into the device chamber to control a quality of the vapor;
   directing the vapor to a tissue wall such that the therapeutic heat is applied to the tissue wall to damage the tissue; and
   applying sufficient therapeutic heat to the tissue wall to induce shrinkage or collapse of the tissue wall.

2. The method of claim 1 wherein directing the vapor to the tissue wall comprises directing the vapor to an airway wall.

3. The method of claim 1 wherein directing the vapor to the tissue wall comprises directing the vapor to a blood vessel wall.

4. The method of claim 1 wherein directing the vapor to the tissue wall comprises directing the vapor to a fallopian tube wall.

5. The method of claim 1 wherein the vapor comprises a superheated vapor.

6. The method of claim 1 wherein the vapor comprises water vapor.

7. The method of claim 1 wherein directing the vapor to the tissue wall comprises inserting a working end of a vapor delivery tool adjacent to the tissue wall.

8. The method of claim 7 wherein the vapor delivery tool comprises a flexible catheter.

9. The method of claim 7 wherein the vapor delivery tool comprises a rigid introducer.

10. The method of claim 7 wherein generating the vapor comprises generating the vapor proximally to a working end of the vapor delivery tool.

* * * * *